US010363034B2

(12) United States Patent
Scirica et al.

(10) Patent No.: US 10,363,034 B2
(45) Date of Patent: *Jul. 30, 2019

(54) GRASPING JAW MECHANISM

(71) Applicant: Covidien LP, Mansfield, MA (US)

(72) Inventors: Paul Scirica, Huntington, CT (US); John Beardsley, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 508 days.

This patent is subject to a terminal disclaimer.

(21) Appl. No.: 15/198,820

(22) Filed: Jun. 30, 2016

(65) Prior Publication Data

US 2016/0310137 A1    Oct. 27, 2016

Related U.S. Application Data

(63) Continuation of application No. 13/852,518, filed on Mar. 28, 2013, now Pat. No. 9,393,016, which is a
(Continued)

(51) Int. Cl.
*A61B 17/068* (2006.01)
*A61B 17/072* (2006.01)
(Continued)

(52) U.S. Cl.
CPC ...... *A61B 17/0686* (2013.01); *A61B 17/0682* (2013.01); *A61B 17/07207* (2013.01);
(Continued)

(58) Field of Classification Search
CPC ............ A61B 17/0686; A61B 17/0682; A61B 17/07207; A61B 2017/00367;
(Continued)

(56) References Cited

U.S. PATENT DOCUMENTS 4,471,781 A    9/1984 Di Giovanni et al.
5,290,299 A    3/1994 Fain et al.
(Continued)

FOREIGN PATENT DOCUMENTS

EP    1908410 A1    4/2008
WO    2004112618 A2    12/2004
WO    2005037329 A2    4/2005

OTHER PUBLICATIONS

European Search Report for EP 07253976.0-2310 date of completion is Jan. 28, 2008 (9 pages).
(Continued)

*Primary Examiner* — Michelle Lopez

(57) ABSTRACT

A surgical device is disclosed which includes a handle assembly, an elongated member and a disposable loading unit. The handle assembly includes a mode selection mechanism configured to alternate the surgical device between a first grasping mode of operation and a second clamping mode of operation. The handle assembly includes a rotation control member and an articulation lever. The rotation control member is configured to facilitate rotation of the elongated member with respect to the handle assembly. The articulation lever is configured to facilitate articulation of the tool assembly about an axis substantially perpendicular to the longitudinal axis of elongated member. In one embodiment, the tool assembly includes a cartridge assembly having a plurality of staples and an anvil assembly configured to clamp and staple tissue in the second clamping mode of operation of the device.

10 Claims, 30 Drawing Sheets

Related U.S. Application Data continuation of application No. 13/155,454, filed on Jun. 8, 2011, now Pat. No. 8,424,736, which is a continuation of application No. 12/353,607, filed on Jan. 14, 2009, now Pat. No. 7,967,178, which is a continuation-in-part of application No. 12/200,057, filed on Aug. 28, 2008, now Pat. No. 7,963,431, which is a continuation-in-part of application No. 11/544,061, filed on Oct. 6, 2006, now Pat. No. 8,336,751.

(60) Provisional application No. 61/062,389, filed on Jan. 25, 2008, provisional application No. 60/967,041, filed on Aug. 31, 2007.

(51) Int. Cl.
A61B 17/00 (2006.01)
A61B 17/29 (2006.01)

(52) U.S. Cl.
CPC ........... *A61B 2017/00367* (2013.01); *A61B 2017/2919* (2013.01); *A61B 2017/2927* (2013.01); *A61B 2017/2929* (2013.01)

(58) Field of Classification Search
CPC .... A61B 2017/2919; A61B 2017/2927; A61B 2017/2929
USPC ..................................................... 227/175.4
See application file for complete search history.

(56) References Cited

U.S. PATENT DOCUMENTS

| | | |
|---|---|---|
| 5,307,976 A | 5/1994 | Olson et al. |
| 5,336,229 A | 8/1994 | Noda |
| 5,344,061 A | 9/1994 | Crainich |
| 5,383,881 A | 1/1995 | Green et al. |
| 5,403,312 A | 4/1995 | Yates et al. |
| 5,405,073 A | 4/1995 | Porter |
| 5,431,669 A | 7/1995 | Thompson et al. |
| 5,452,836 A | 9/1995 | Huitema et al. |
| 5,465,894 A | 11/1995 | Clark et al. |
| 5,465,895 A | 11/1995 | Knodel et al. |
| 5,487,500 A | 1/1996 | Knodel et al. |
| 5,529,235 A | 6/1996 | Boiarski et al. |
| 5,547,117 A | 8/1996 | Hamblin et al. |
| 5,553,765 A | 9/1996 | Knodel et al. |
| 5,597,107 A | 1/1997 | Knodel et al. |
| 5,605,272 A | 2/1997 | Witt et al. |
| 5,632,432 A | 5/1997 | Schulze et al. |
| 5,643,289 A | 7/1997 | Sauer et al. |
| 5,697,543 A | 12/1997 | Burdorff |
| 5,706,997 A | 1/1998 | Green et al. |
| 5,713,505 A | 2/1998 | Huitema |
| 5,762,255 A | 6/1998 | Chrisman et al. |
| 5,814,055 A | 9/1998 | Knodel et al. |
| 5,823,066 A | 10/1998 | Huitema et al. |
| 5,855,311 A | 1/1999 | Hamblin et al. |
| 6,109,500 A * | 8/2000 | Alli .................. A61B 17/07207 227/175.2 |
| H1904 H | 10/2000 | Yates et al. |
| 6,592,597 B2 | 7/2003 | Grant et al. |
| 6,656,193 B2 | 12/2003 | Grant et al. |
| 6,743,240 B2 | 6/2004 | Smith et al. |
| 6,755,338 B2 | 6/2004 | Hahnen et al. |
| 6,786,382 B1 | 9/2004 | Hoffman |
| 6,805,273 B2 | 10/2004 | Bilotti et al. |
| 6,824,548 B2 | 11/2004 | Smith et al. |
| 6,843,794 B2 | 1/2005 | Sixto, Jr. et al. |
| 6,905,057 B2 | 6/2005 | Swayze et al. |
| 6,945,979 B2 | 9/2005 | Kortenbach et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,981,628 B2 | 1/2006 | Wales |
| 6,988,649 B2 | 1/2006 | Shelton, IV et al. |
| 6,988,650 B2 | 1/2006 | Schwemberger et al. |
| 7,000,818 B2 | 2/2006 | Shelton, IV et al. |
| 7,000,819 B2 | 2/2006 | Swayze et al. |
| 7,121,446 B2 | 10/2006 | Arad et al. |
| 7,159,750 B2 | 1/2007 | Racenet et al. |
| 7,328,829 B2 | 2/2008 | Arad et al. |
| 7,963,431 B2 | 6/2011 | Scirica |
| 7,967,178 B2 | 6/2011 | Scirica et al. |
| 8,424,736 B2 | 4/2013 | Scirica et al. |
| 8,708,210 B2 * | 4/2014 | Zemlok .............. A61B 17/2909 227/175.1 |
| 8,973,803 B2 * | 3/2015 | Hall ................ A61B 17/07207 227/175.1 |
| 2002/0099388 A1 | 7/2002 | Mayenberger |
| 2002/0188294 A1 * | 12/2002 | Couture ............. A61B 18/1445 606/51 |
| 2002/0198537 A1 | 12/2002 | Smith et al. |
| 2003/0009193 A1 | 1/2003 | Corsaro |
| 2003/0191478 A1 | 10/2003 | Kortenbach et al. |
| 2004/0193185 A1 | 9/2004 | McBrayer |
| 2004/0193186 A1 | 9/2004 | Kortenbach et al. |
| 2004/0199180 A1 | 10/2004 | Knodel et al. |
| 2004/0199181 A1 | 10/2004 | Knodel et al. |
| 2004/0232195 A1 | 11/2004 | Shelton et al. |
| 2004/0232199 A1 | 11/2004 | Shelton et al. |
| 2004/0232201 A1 | 11/2004 | Wenchell et al. |
| 2005/0006431 A1 | 1/2005 | Shelton et al. |
| 2005/0006432 A1 | 1/2005 | Racenet et al. |
| 2005/0006434 A1 | 1/2005 | Wales et al. |
| 2005/0070925 A1 | 3/2005 | Shelton et al. |
| 2005/0072827 A1 | 4/2005 | Mollenauer |
| 2005/0103819 A1 | 5/2005 | Racenet et al. |
| 2005/0139632 A1 | 6/2005 | Schwemberger et al. |
| 2005/0139633 A1 | 6/2005 | Wukusick et al. |
| 2005/0139634 A1 | 6/2005 | Schwemberger et al. |
| 2005/0139635 A1 | 6/2005 | Wukusick et al. |
| 2005/0139636 A1 | 6/2005 | Schwemberger et al. |
| 2005/0143759 A1 | 6/2005 | Kelly |
| 2005/0145672 A1 | 7/2005 | Schwemberger et al. |
| 2005/0145673 A1 | 7/2005 | Nguyen et al. |
| 2005/0165415 A1 | 7/2005 | Wales |
| 2005/0173490 A1 | 8/2005 | Shelton |
| 2005/0178813 A1 | 8/2005 | Swayze et al. |
| 2005/0187576 A1 | 8/2005 | Whitman et al. |
| 2005/0247752 A1 | 11/2005 | Kelly et al. |
| 2005/0247753 A1 | 11/2005 | Kelly et al. |
| 2005/0263562 A1 | 12/2005 | Shelton et al. |
| 2006/0000867 A1 | 1/2006 | Shelton et al. |
| 2006/0000868 A1 | 1/2006 | Shelton et al. |
| 2006/0022014 A1 | 2/2006 | Shelton et al. |
| 2006/0022015 A1 | 2/2006 | Shelton et al. |
| 2006/0049230 A1 | 3/2006 | Shelton et al. |
| 2006/0124689 A1 * | 6/2006 | Arad ................ A61B 17/07207 227/176.1 |
| 2007/0034670 A1 | 2/2007 | Racenet et al. |
| 2007/0060952 A1 | 3/2007 | Roby et al. |
| 2008/0314958 A1 | 12/2008 | Scirica |
| 2011/0240713 A1 | 10/2011 | Scirica et al. |
| 2011/0272448 A1 | 11/2011 | Scirica et al. |
| 2012/0241497 A1 * | 9/2012 | Mandakolathur Vasudevan ......... A61B 17/00491 227/176.1 |
| 2015/0297216 A1 * | 10/2015 | Williams ......... A61B 17/07207 227/175.2 |

OTHER PUBLICATIONS

European Search Report for EP 09250137 date of completion is Apr. 29, 2009.
European Search Report for EP 12154546.1-2310 date of completion is Oct. 18, 2012 (7 pages).
Australian Examination Report from Appl. No. 2014221280 dated Oct. 7, 2015.

(56) References Cited

OTHER PUBLICATIONS

Canadian Office Action from Appln. No. 2,895,725 dated Jul. 12, 2016.

* cited by examiner

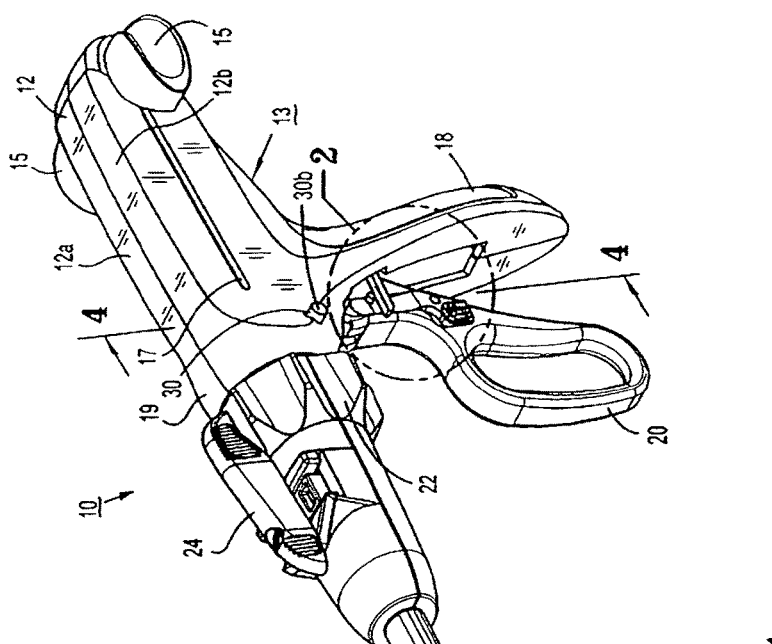
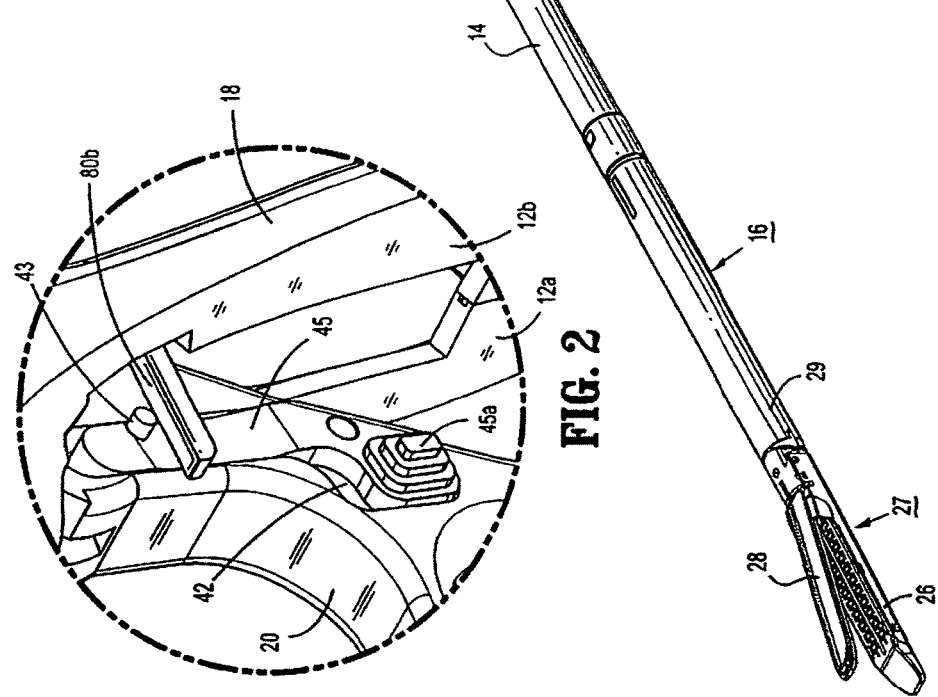
FIG. 1
FIG. 2

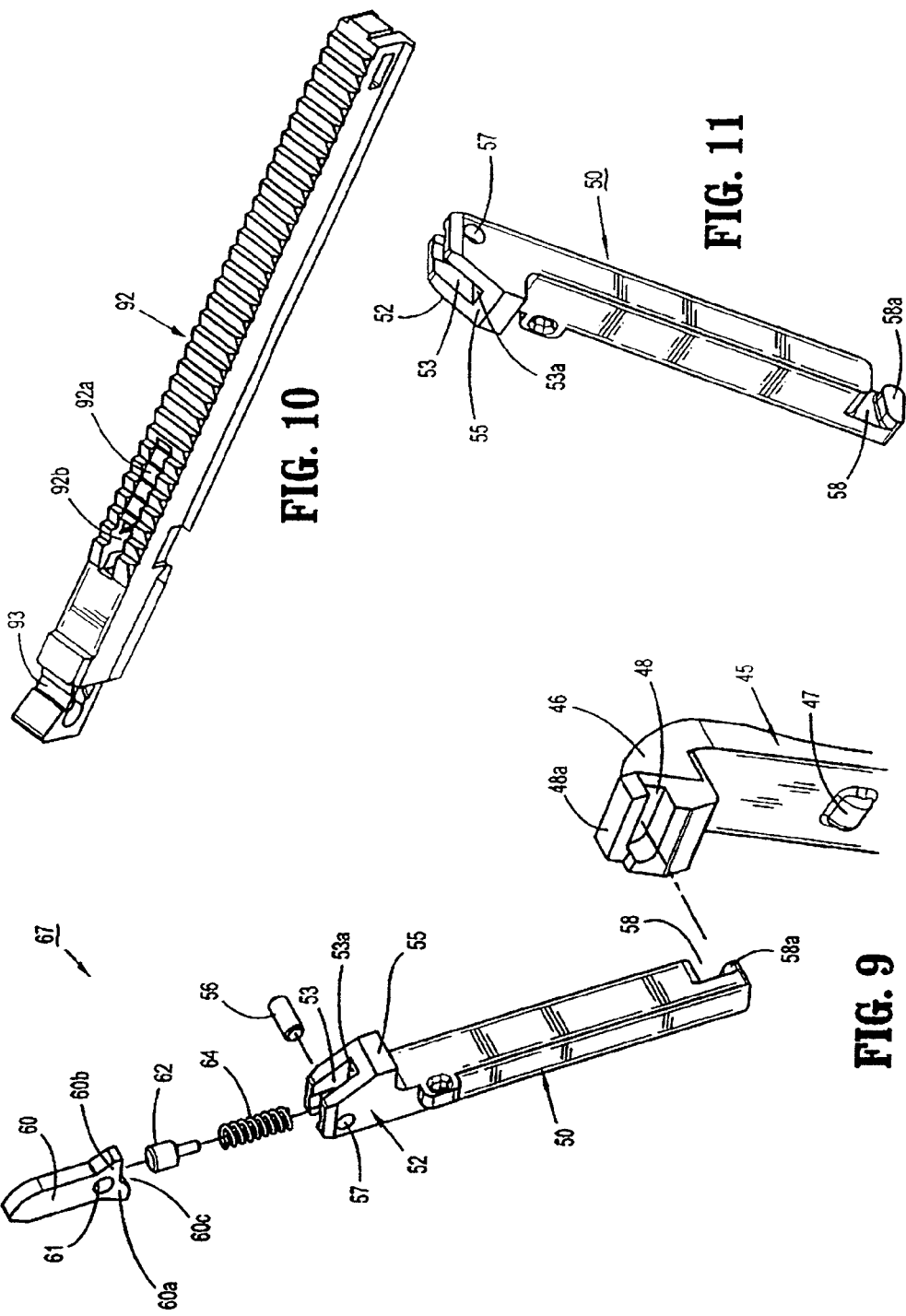

GRASPING JAW MECHANISM

CROSS-REFERENCE TO RELATED APPLICATIONS

This application is a continuation of U.S. patent application Ser. No. 13/852,518, filed Mar. 28, 2013, which is a continuation of U.S. patent application Ser. No. 13/155,454 filed Jun. 8, 2011, now U.S. Pat. No. 8,424,736, which claims the benefit of and priority to U.S. Provisional Application Ser. No. 61/062,389, filed Jan. 25, 2008. U.S. patent application Ser. No. 13/155,454, filed Jun. 8, 2011, is a continuation of U.S. patent application Ser. No. 12/353,607, filed Jan. 14, 2009, now U.S. Pat. No. 7,967,178 and is also a Continuation-in-part of U.S. patent application Ser. No. 12/200,057 filed Aug. 28, 2008, now U.S. Pat. No. 7,963,431, which claims the benefit of priority to U.S. Provisional Application Ser. No. 60/967,041 filed Aug. 31, 2007 and is a Continuation-in-part of U.S. patent application Ser. No. 11/544,061 filed Oct. 6, 2006, now U.S. Pat. No. 8,336,751, all of which are incorporated herein in its entirety by reference.

BACKGROUND

1. Technical Field

The present disclosure relates to a surgical stapling device and, more particularly, to an endoscopic surgical stapling device configured to operate a tool assembly in a grasping mode independent of a clamping and/or firing mode.

2. Background of Related Art

Surgical devices wherein tissue is first grasped or clamped between opposing jaw structure and then joined by surgical fasteners are well known in the art. The fasteners are typically in the form of surgical staples, but two-part polymeric fasteners can also be utilized.

Instruments for this purpose can include a tool assembly with two elongated members which are respectively used to capture or clamp tissue. Typically, one of the members carries a staple cartridge which houses a plurality of staples arranged, for example, in at least two lateral rows while the other member has an anvil that defines a surface for forming the staple legs as the staples are driven from the staple cartridge. In some staplers, the stapling operation is effected by cam bars that travel longitudinally through the staple cartridge, with the cam bars acting upon staple pushers for sequentially ejecting the staples from the staple cartridge. A knife can travel between the staple rows for longitudinally cutting the stapled tissue between the rows of staples. Such staplers are disclosed in U.S. Pat. Nos. 6,250,532 and 6,241,139, each of which are currently owned by Tyco Healthcare Group LP, and are incorporated herein by reference in their entirety.

In endoscopic or laparoscopic procedures, surgery is performed through small incisions or through small diameter cannulas inserted through small entrance wounds in the skin. Due to the limited degree of motion of an instrument when it is positioned through the skin, it may be quite difficult for a surgeon to manipulate the tool assembly of the instrument around body tissue to access and/or clamp the tissue site. Instruments having rotatable endoscopic body portions and rotatable and/or articulatable tool assemblies have been developed to overcome this problem and are commercially available. Although these instruments provide significant improvements in the endoscopic tool art, further improvements that may decrease the time required for surgical procedures and allow easier access to tissue sites are desired.

Accordingly, a continuing need exists for an endoscopic or laparoscopic surgical device having a tool assembly which can be quickly and easily manipulated between different modes of operation.

SUMMARY

In accordance with the present disclosure, a surgical stapling device is provided which includes a handle assembly having a movable handle, an elongated member, and a disposable loading unit ("DLU"). The DLU includes a tool assembly positioned at a distal end having an anvil assembly and a cartridge assembly. The elongated member is rotatably secured to the handle assembly. The tool assembly is a stapling device and the handle assembly includes a grasping pawl which is movable into engagement with an actuation shaft or actuation member to allow the tool assembly to be operated in a grasper mode. More specifically, the grasping pawl is manipulated by a pair of slide buttons slidably positioned on opposed sides of the handle assembly and is selectively movable into engagement with the actuation shaft to allow the actuation shaft to move a distance which will, upon operation of the movable handle, effect approximation of cartridge and anvil assemblies of the tool assembly, but will not affect the firing of staples.

In another aspect of the disclosure, a rotation control member is rotatably mounted to the forward end of the handle assembly to facilitate rotation of elongated member with respect to the handle assembly.

In another aspect of the present disclosure, a surgical device comprises an end effector; an endoscopic shaft defining a longitudinal axis; and a handle assembly. The handle assembly comprises a longitudinally movable actuation member and a pivotable handle having an engagement member movably mounted with respect to the pivotable handle and arranged to pivot with the pivotable handle. The device also includes a depressible button arranged to engage the engagement member and move the engagement member between a first position in which the engagement member moves the actuation member longitudinally and a second position in which the engagement member does not move the actuation member.

The engagement member, in certain embodiments, has an arm slidably mounted on the pivotable handle and a pawl pivotably mounted with respect to the arm. The actuation member has a plurality of teeth and the pawl slides over the teeth when the engagement member is in the second position. The pawl engages the teeth when the engagement member is in the first position.

The handle assembly may have an advancement pawl movable with the pivotable handle and biased into engagement with the actuation member. The advancement pawl is arranged to engage teeth of the actuation member and move the actuation member longitudinally when the engagement member is in the second position.

The surgical device in certain embodiments has a locking member biased into engagement with the actuation member, to prevent longitudinal movement of the actuation member. A disconnect assembly having an angled stepped portion is arranged to engage the locking member and move the locking member away from the actuation member. The disconnect assembly includes a first link, having the angled stepped portion, and a second link pivotably attached to the first link at a first end and pivotably attached to the pivotable handle at a second end of the second link. The first link and the second link are dimensioned so that the angled stepped portion does not engage the locking member when the engagement member is in the first position.

In yet another aspect of the disclosure, an articulation lever is mounted adjacent the rotation control member to facilitate articulation of the tool assembly.

BRIEF DESCRIPTION OF THE DRAWINGS

Embodiments of the presently disclosed surgical stapling device are disclosed herein with reference to the drawings wherein:

FIG. 1 is a side perspective view of the presently disclosed surgical stapling device;

FIG. 2 is an enlarged view of the indicated area of detail shown in FIG. 1;

FIG. 9 is an enlarged view of the indicated area of detail shown in FIG. 3;

FIG. 10 is a bottom perspective view of the toothed rack of FIG. 3;

FIG. 11 is a side perspective view of the grasping pawl arm rotated 90. degree. from the depiction shown in FIG. 9;

DETAILED DESCRIPTION OF THE EMBODIMENTS

Figure 3:
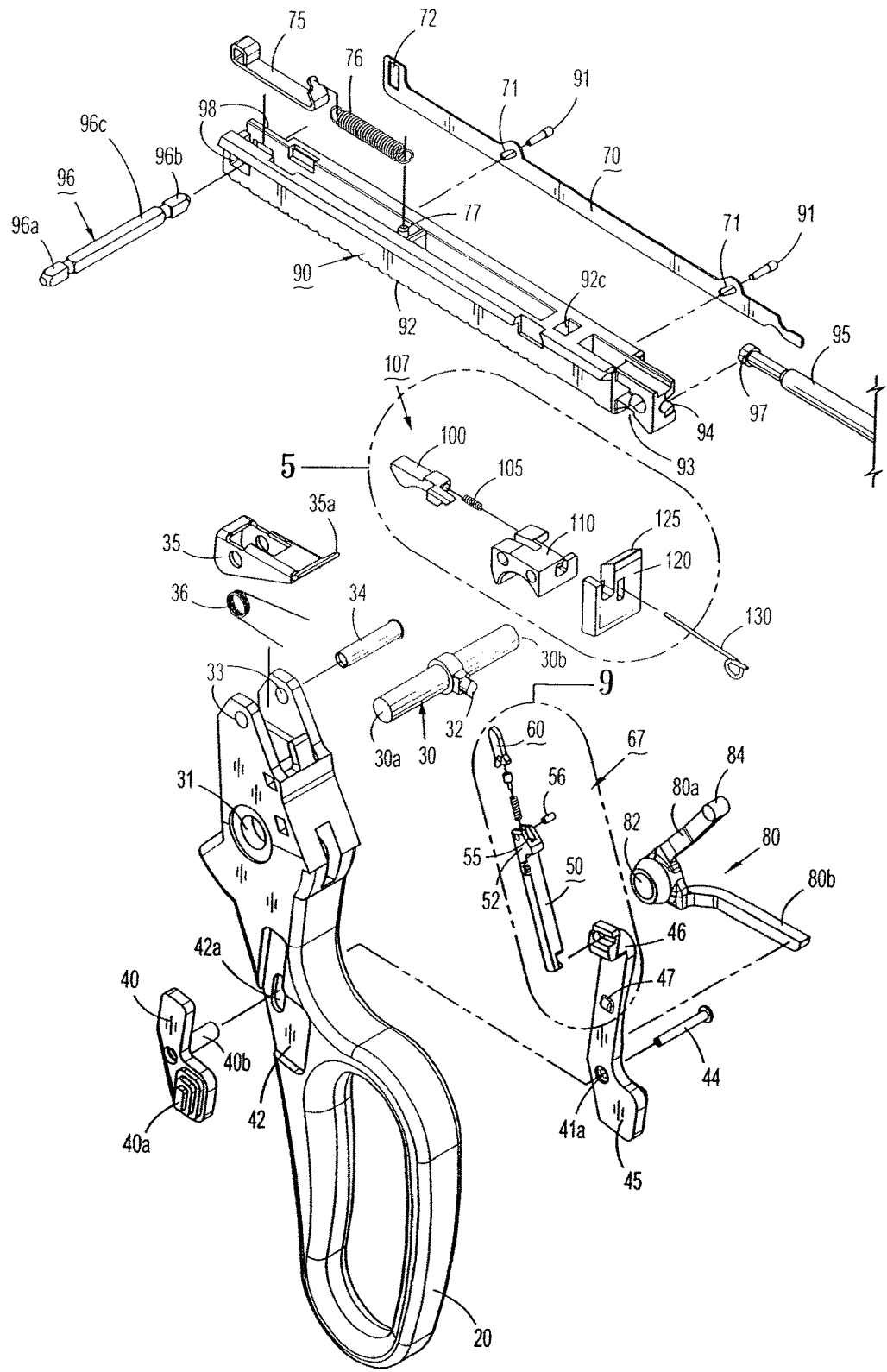
FIG. 3 is a side perspective view of the proximal end of the surgical stapling device shown in FIG. 1, with parts separated.

Embodiments of the presently disclosed grasping jaw mechanism will now be described in detail with reference to the drawings in which like reference numerals designate identical or corresponding element in each of the several views.

Throughout this description, the term "proximal" will refer to the portion of the device closest to the operator and the term "distal" will refer to the portion of the device furthest from the operator.

FIG. 1 illustrates one embodiment of the presently disclosed surgical stapling device shown generally as 10. Surgical stapling device 10 includes a handle assembly 13, an elongated member 14 extending distally from handle assembly 13, and a disposable loading unit ("DLU") 16 releasably secured to a distal end of elongated member 14. DLU 16 includes a proximal body portion 29 which forms an extension of elongated member 14, and a distal tool assembly 27 including a cartridge assembly 26 and an anvil assembly 28. Cartridge assembly 26 and anvil assembly 28 further define a pair of jaws. Tool assembly 27 is pivotally connected to body portion 29 about an axis substantially perpendicular to the longitudinal axis of elongated member 14. Cartridge assembly 26 houses a plurality of staples. Anvil assembly 28 is movable in relation to cartridge assembly 26 between an open position spaced from cartridge assembly 26 and an approximated or clamped position in juxtaposed alignment with cartridge assembly 26. Tool assembly 27 may alternatively be arranged such that cartridge assembly 26 is movable in relation to anvil assembly 28. DLU 16 is configured to apply linear rows of staples measuring from about 30 mm to about 60 mm in length. DLU's having linear rows of staples of other lengths are also envisioned, e.g., 45 mm.

Handle assembly 13 includes a stationary handle 18, a movable handle 20, and a barrel portion 19. A rotation control member 22 is rotatably mounted at the forward end of barrel portion 19 to facilitate rotation of elongated member 14 with respect to handle assembly 13. Rotation control member 22 is formed from molded plastic half-sections 12a and 12b, although other materials, e.g., metals, and manufacturing methods are envisioned. An articulation lever 24 is also mounted on the forward end of barrel portion 19 adjacent rotation control member 22 to facilitate articulation of tool assembly 30. U.S. Pat. No. 5,865,361 to Milliman et al., which is owned by Tyco Healthcare, LP, describes a rotation control assembly and articulation assembly for a surgical stapling apparatus and is hereby incorporated herein by reference in its entirety.

A pair of retractor knobs 15 is movably positioned along barrel portion 19 to return device 10 to a retracted position, as will be described in detail below (see FIG. 1). A pair of recesses 42 and 48 (see FIG. 2) in opposed lateral faces of movable handle 20 are dimensioned for slidably receiving slide buttons 40 and 45, respectively (see FIG. 3). Slide button 40 is operatively associated with slide button 45, such that movement of one effects movement of the other. Slide buttons 40 and 45 are configured to alternate device 10 between a "grasping" mode and a "firing" or clamping mode. In grasping mode, tool assembly 27 is configured to operate as a grasping jaw mechanism, i.e., anvil assembly 28 is movable in relation to cartridge assembly 26 to grasp tissue therebetween, back and forth between open and approximated positions. In clamping mode, tool assembly 27 is configured to operate as a clamping mechanism, i.e., anvil assembly 28 is movable in relation to cartridge assembly 26 to grasp tissue therebetween and apply linear rows of staples. In the clamping mode, the user must retract retractor knobs 15 to open tool assembly 27 and release the tissue. Slide buttons 40 and 45 each include a raised surface 40a and 45a, respectively. Raised surfaces 40a and 45a are configured to be engaged by the surgeon's finger to move slide buttons 40 and 45 within recesses 42 and 48, respectively. As to be appreciated, alternatives to slide buttons 40 and 45 are also contemplated, e.g., knobs, levers, depressible buttons, toggles, trigger assemblies, etc.

Handle assembly 13 includes a housing 12 formed from a pair of molded half-sections 12a and 12b, which forms stationary handle 18 and barrel portion 19 of handle assembly 13. Half-sections 12a and 12b are formed of a thermoplastic material, e.g., polycarbonate. Alternately, other materials having the requisite strength requirements may be used to form housing 12, e.g., surgical grade metals. Housing 12 half-sections 12a and 12b are secured to each other using known fastening techniques, e.g., adhesives, welding, interlocking structure, screws, etc. Alternately, other fastening techniques may be used.

Referring to FIG. 3, movable handle 20 is rotatably supported between housing half-sections 12a and 12b about a cylindrical member (not shown) which is received within an opening 31 within movable handle 20. A biasing member (not shown), e.g., a torsion spring, may be included to urge movable handle 20 away from stationary handle 18 to a non-compressed position. Movable handle 20 includes a pair of throughbores 33 dimensioned to receive a pivot member 34. An advancement pawl 35 is rotatably supported on pivot member 34 and is biased by a spring 36 towards an actuation shaft 90.

Actuation member or actuation shaft 90 is slidably supported between retracted and advanced positions within barrel portion 19 of housing 12 and includes a distal end defining a recess 94 configured to rotatably receive the proximal end 97 of a control rod 95. Actuation shaft 90 includes a toothed rack 92. Advancement pawl 35 has an engagement finger 35a which is biased by spring 36 towards toothed rack 92 of actuation shaft 90. When movable handle 20 is actuated, i.e., is pivoted towards stationary handle 18 against the bias of a torsion spring (not shown), engagement finger 35a of pawl 35 engages toothed rack 92 of actuation shaft 90 to advance actuation shaft 90 and control rod 95 distally.

Figure 15:
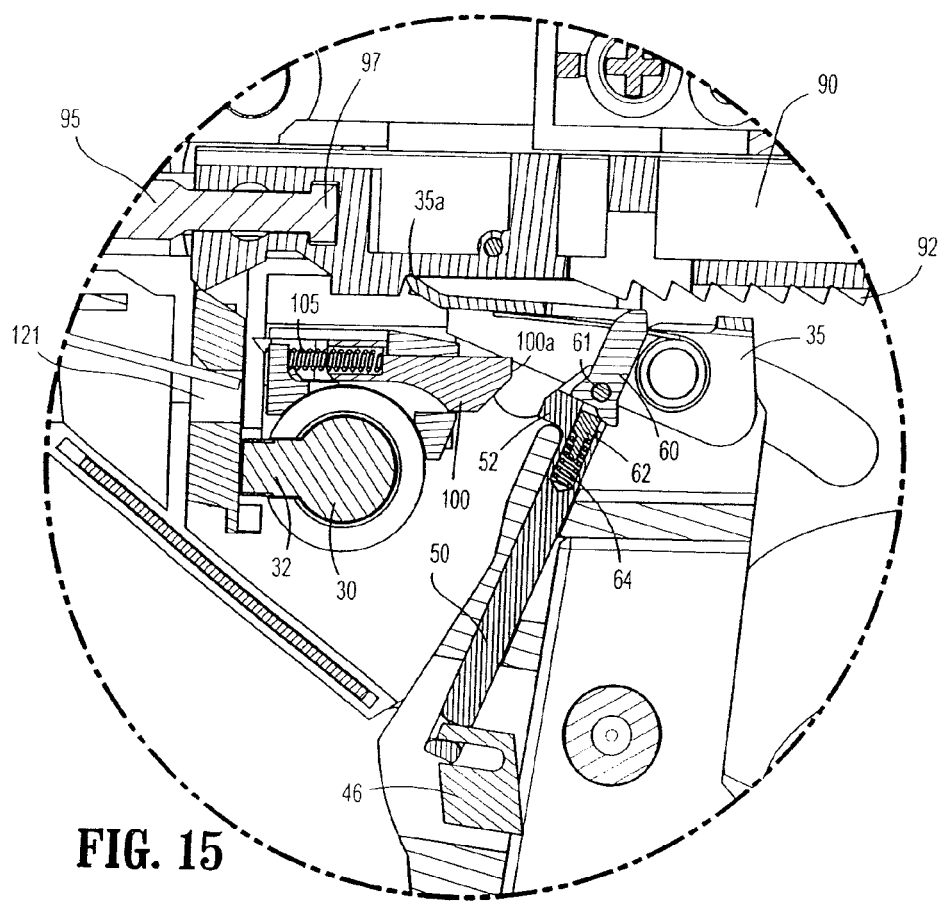
FIG. 15 is an enlarged view of the indicated area of detail shown in FIG. 14, illustrating the handle assembly in clamping/firing mode.
Figure 16:
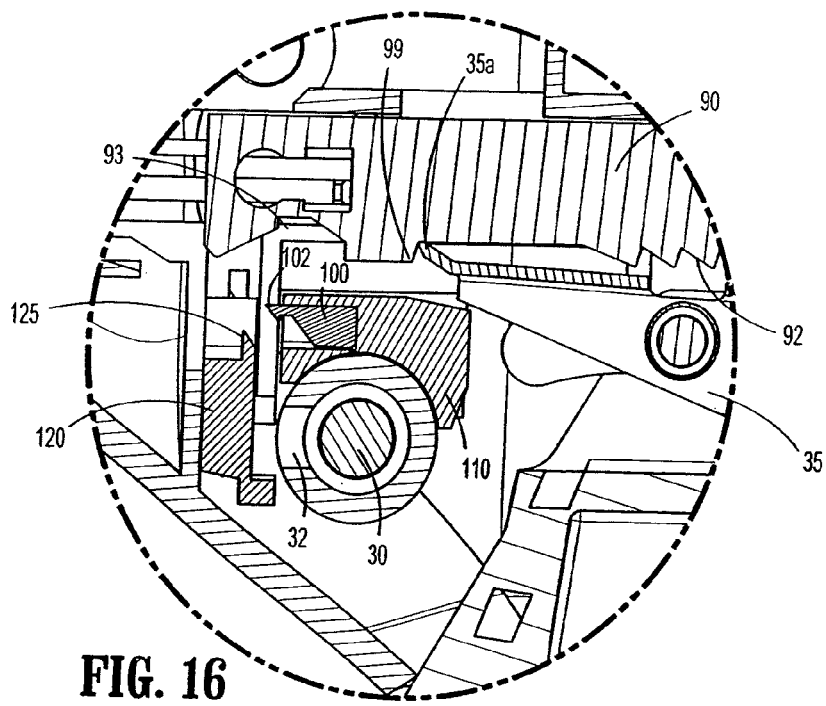
FIG. 16 is a side cross-sectional view taken along section line 16-16 of FIG. 4.

Referring to FIGS. 3 and 5-8, a vertical pawl 120 is a pawl, plate, or other engagement member or locking member slidably positioned in a slot 121 (see FIG. 15) defined between housing half-sections 12a and 12b. Vertical pawl 120 is movable from an extended or upward position in which the tip 125 of vertical pawl 120 engages a cutout 93 formed in the distal end of actuation shaft 90, to a retracted or downward position in which tip 125 of vertical pawl 120 is spaced from actuation shaft 90. A spring 130 supported between housing half-sections 12a and 12b is positioned to bias vertical pawl 120 to the extended position. In the extended position, vertical pawl 120 prevents advancement of actuation shaft 90 to prevent firing of device 10.

A plunger 30 is reciprocally supported between spaced cylindrical channels (not shown) formed in housing half-sections 12a and 12b. Plunger 30 includes a cam member 32. A spring (not shown) may be positioned on each end of plunger 30 within spaced cylindrical channels (not shown) to urge plunger 30 to a position wherein cam member 32 is centrally positioned between a pair of cam surfaces 122 formed on vertical pawl 120 (see FIG. 7). Each cam surface 122 has a recess 124 formed therein for releasably receiving cam member 32 of plunger 30.

Each end 30a of plunger 30 extends through stationary handle 18 and can be pressed against the bias of a spring (not shown) to force cam member 32 into engagement with a respective one of cam surfaces 122 on vertical pawl 120. When cam member 32 is moved into engagement with one of cam surfaces 122, vertical pawl 120 is urged from the extended position to the retracted position to move tip 125 of vertical pawl 120 out of cutout 93 of actuation shall 90 (see FIGS. 19-23). The positioning of cam member 32 in recess 124 of a respective cam surface 122 retains vertical pawl 120 in the retracted position.

Figure 5:
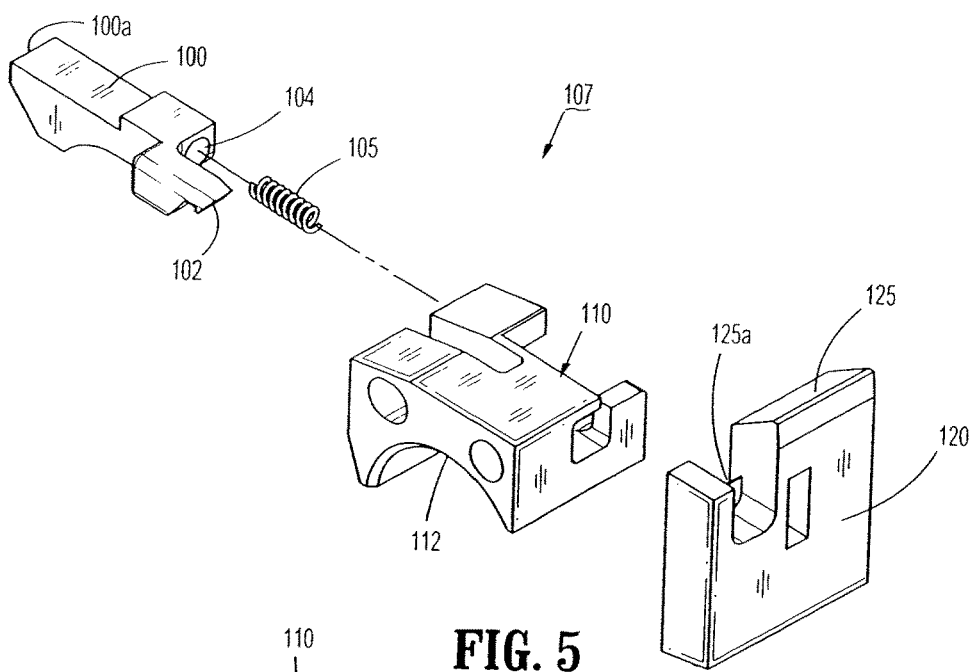
FIG. 5 is an enlarged view of the indicated area of detail shown in FIG. 3.
Figure 6:
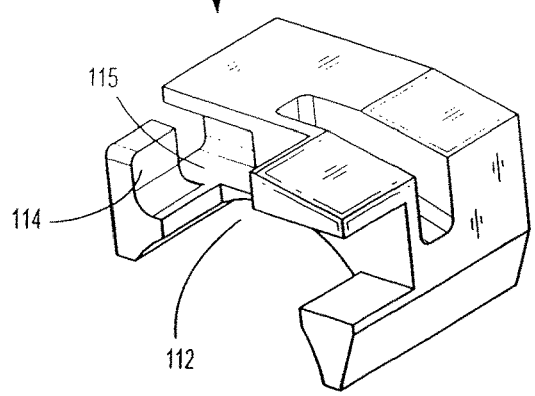
FIG. 6 is a perspective view of the spring support of FIG. 5.
Figure 7:
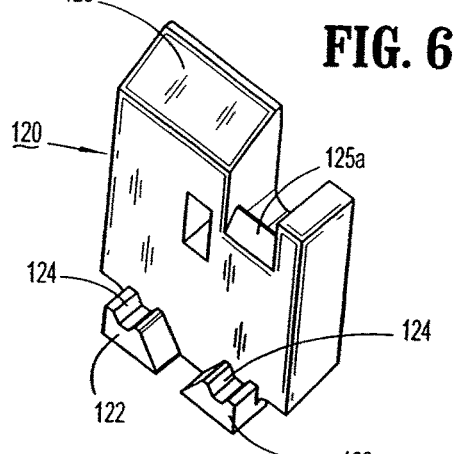
FIG. 7 is a perspective view of the vertical pawl of FIG. 5.
Figure 8:
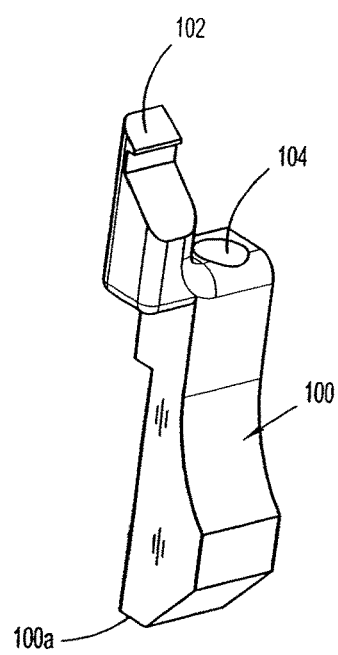
FIG. 8 is a perspective view of the locking cam of FIG. 5.
Figures 12, 13:
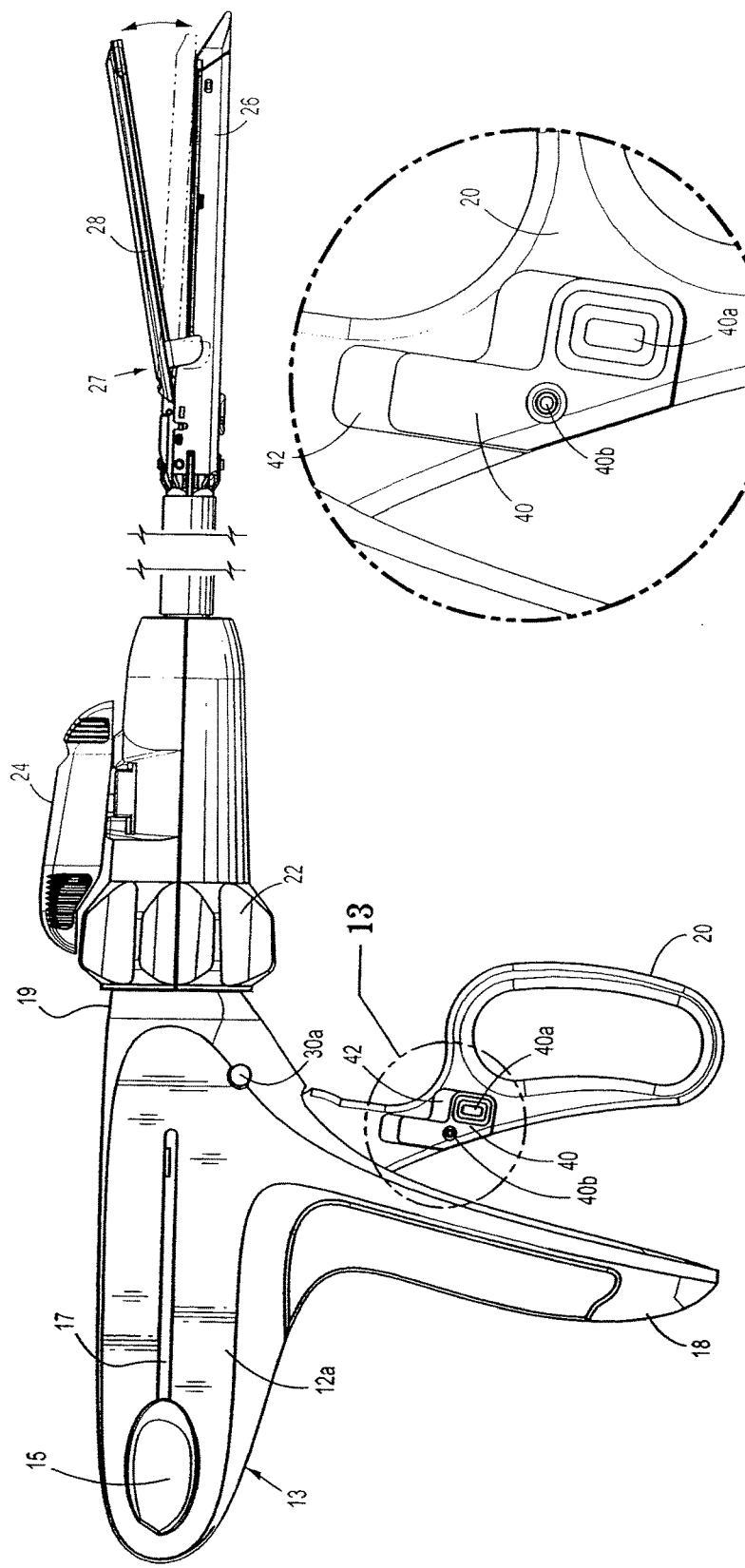
FIG. 12 is a side view of the surgical stapling device shown in FIG. 1.
FIG. 13 is an enlarged view of the indicated area of detail shown in FIG. 12.

Referring to FIGS. 3 and 5, a locking cam assembly 107 is supported between retracted and advanced positions within barrel portion 19 of housing 12 (see FIG. 1) and includes a spring support 110 and a cam member 100 having a tip 102 and a proximal surface 100a. Plunger 30 is received within an annular recess 112, shown in FIGS. 3 and 5, defined in a bottom side of spring support 110 to maintain spring support 110 between housing half-sections 12a and 12b. Cam member 100 is slidably received in a slot 115 defined in spring support 110. Cain member 100 is movable from an extended or distal position in which tip 102 of cam member 100 engages tip 125 of vertical pawl 120, to a retracted or proximal position in which tip 102 of cam member 100 is spaced from vertical pawl 120. In the retracted position, surface 100a of cam member 100 is spaced from spring support 110. Cam member 100 is biased proximally by a spring 105 which is secured at one end to a recess 104 defined in the distal end of cam member 100 and is configured at the opposite end to engage an extension 114 formed by slot 115 in spring support 110. In the extended or distal position, tip 102 of cam member 100 engages tip 125 of vertical pawl 120 to retain vertical pawl 120 in the retracted position.

Referring to FIGS. 3, 9, and 11, movable handle 20 includes a grasping pawl assembly 67 operatively associated with slide buttons 40 and 45. Grasping pawl assembly 67 is configured for movement with respect thereto in response to manipulation of slide buttons 40 and 45. Grasping pawl assembly 67 includes a slider or other engagement member such as pawl arm 50 and grasping pawl 60. Pawl arm 50 has a sloped surface 55 defined on an outturned portion 52 of a top end of pawl arm 50, and grasping pawl 60 is pivotally supported within outturned portion 52 of pawl arm 50. A top end of slide button 45 includes an in-turned portion 46 having an extension 48a that defines a recessed groove 48. Recessed groove 48 is dimensioned and configured to slidably receive an extension 58a defined by a recessed groove 58 in a bottom end of pawl arm 50. Reciprocally, recessed groove 58 in pawl arm 50 is dimensioned and configured for slidably receiving extension 48a of slide button 45. A bottom end of slide button 45 includes an opening 41a configured to receive a connector pin 44 therethrough. A cylindrical receptacle 40b extends outwardly from an inner surface of slide button 40 and is configured and dimensioned to translate within a longitudinal slot 42a formed in recess 42 of movable handle 20. Connector pin 44 is dimensioned to be received within receptacle 40b to secure slide button 45 to slide button 40. A protrusion 47 is disposed on a lateral surface of slide button 45 configured to be received in a snap-fit manner within a pair of detents 108a and 108b defined within movable handle 20 (see FIG. 4), as will be discussed in further detail below.

Outturned portion 52 of pawl arm 50 includes a recessed groove 53 having a pair of throughbores 57 dimensioned to slidably receive a pivot pin 56. A biasing spring 64 is configured at one end for insertably receiving a pivot pin 62 therein and is insertably received within recessed groove 53 at the other end. Grasping pawl 60 includes a pair of lateral extensions 60b and 60c defining a recess 60a. Pivot pin 56 is received by an opening 61 in a bottom end of grasping pawl 60. Pivot pin 62 is pivotally received within recess 60a, such that grasping pawl 60 is pivotal in a proximal direction about pivot pin 62 in relation to pawl arm 50. Recessed groove 53 is dimensioned to accommodate the pivoted motion of grasping pawl 60 between a straight position, i.e., along the longitudinal axis of pawl arm 50, and a proximal or rearward position. Lateral extension 60b is configured to contact a surface 53a of recessed groove 53, such that the pivoting motion of grasping pawl 60 is restricted to a proximal direction from a straight position with respect to pawl arm 50. Lateral extension 60c is configured to pivot through groove 53 in outturned portion 52 to allow pivoting motion of grasping pawl 60 into the proximal or rearward position. In the proximal or rearward position, lateral extension 60c depresses pivot pin 62, and thus spring 64, within a bore 63 defined in outturned portion 52 (see FIG. 23).

Figure 4:
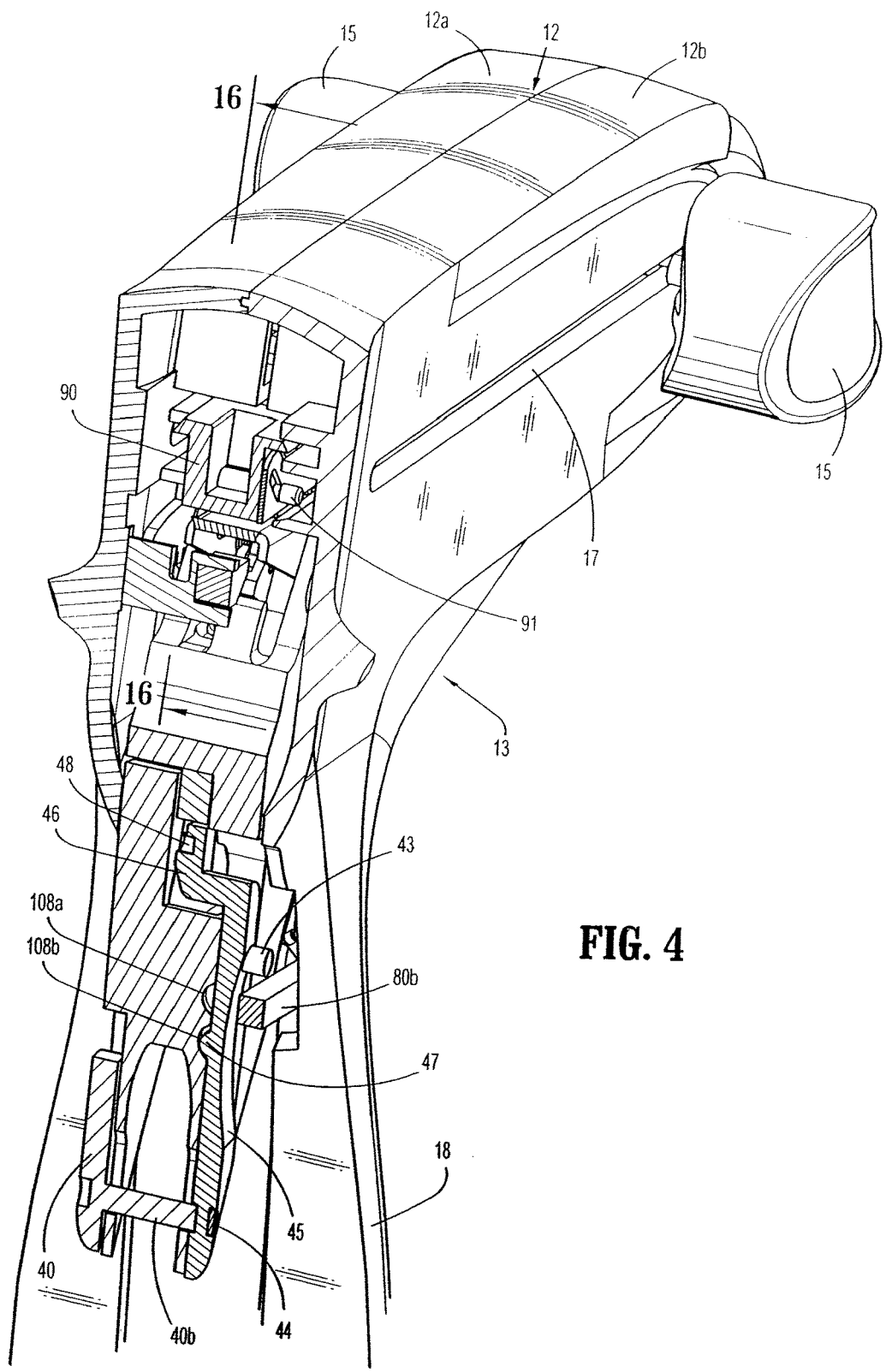
FIG. 4 is a cross-sectional rear perspective view taken along section line 4-4 of FIG. 1.
Figure 17:
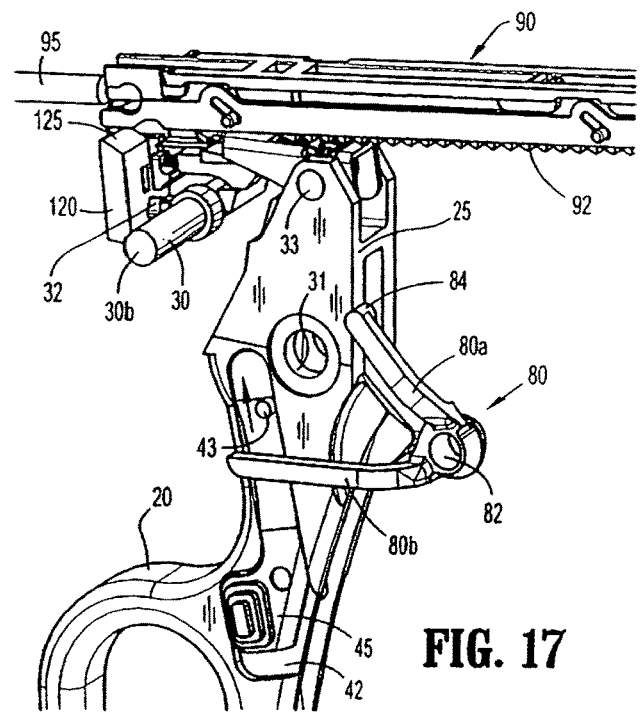
FIG. 17 is a side perspective view with portions broken away of the handle assembly of the surgical stapling device shown in FIG. 1, with the housing removed.
Figure 18:
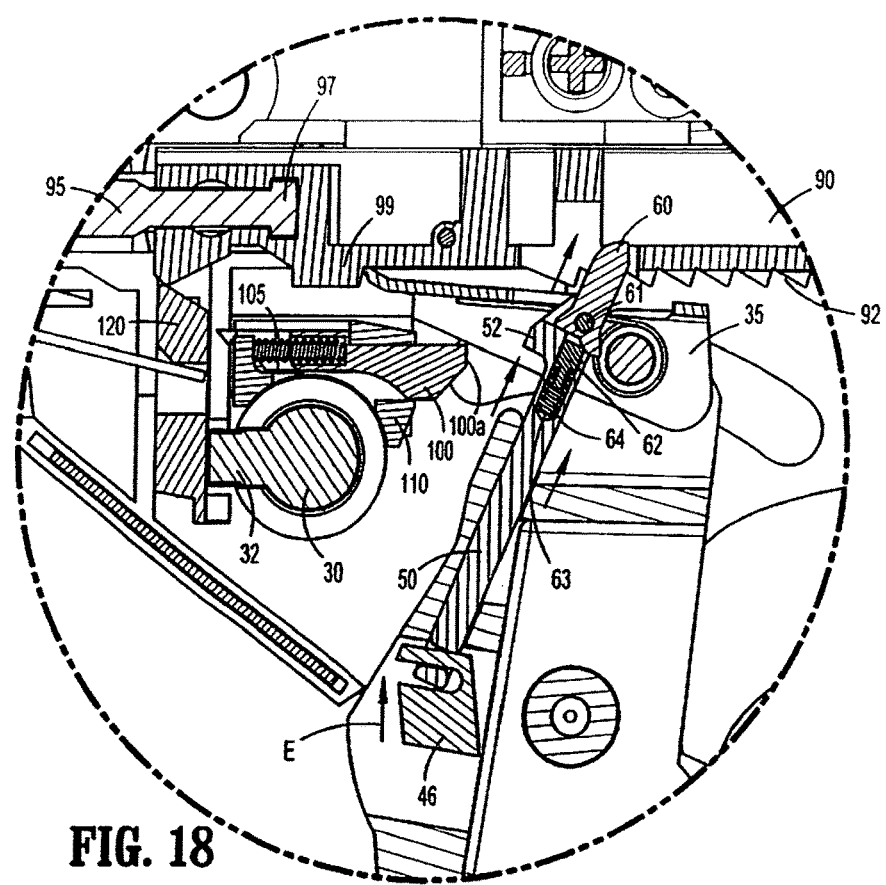
FIG. 18 illustrates the grasping pawl of FIG. 15 engaging the toothed rack.
Figure 23:
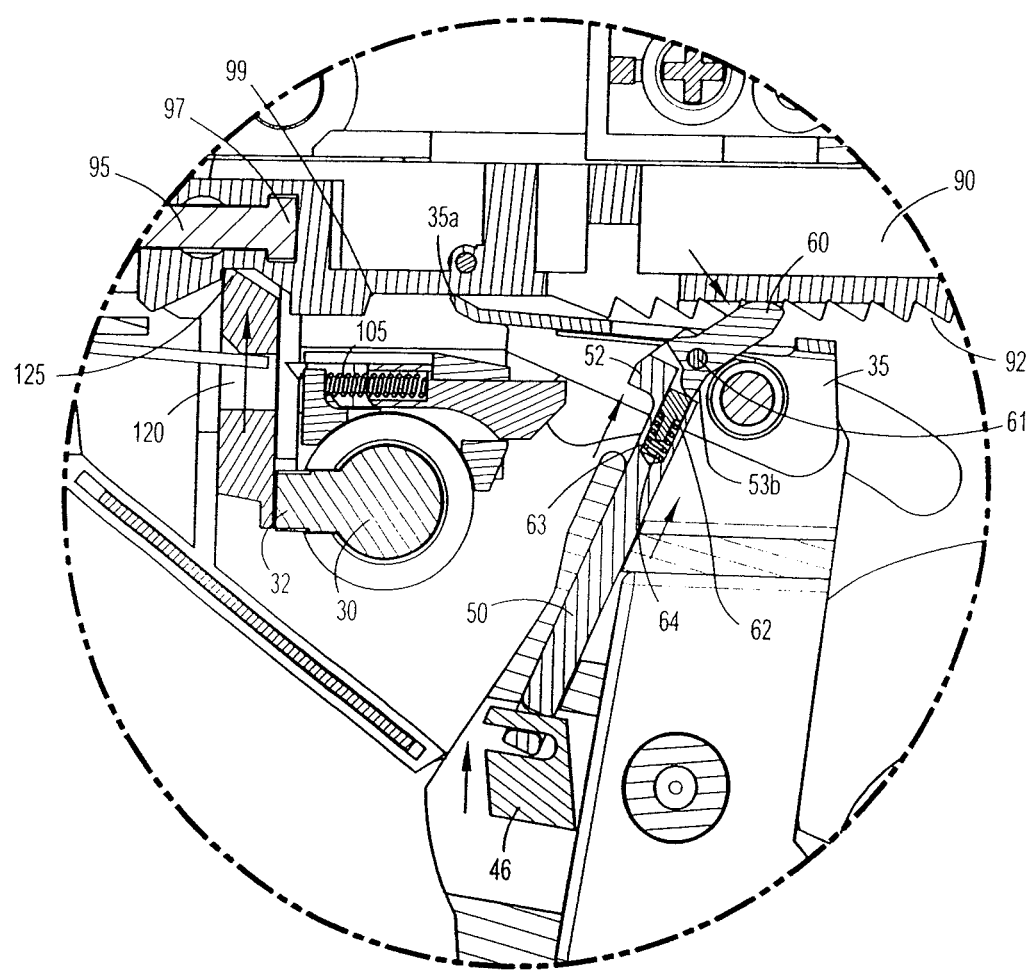
FIG. 23 is a side cross-sectional view, illustrating the vertical pawl in the upward position and slide button in the upward position causing the grasping pawl to engage the toothed rack.

Referring to FIG. 17, handle assembly 13 (see FIG. 1) further includes a yoke 80 configured to return device 10 to the default grasping mode, such that slide buttons 40 and 45 are returned to the upward position to urge grasping pawl 60 into engagement with a slot in the distal end portion of toothed rack 92, as will be discussed in detail below. Yoke 80 is rotatably supported within stationary handle 18 about a cylindrical member (not shown) which is received within an opening 82 within yoke 80. A pair of arms 80a and 80b extend laterally from opening 82. Upon movement of movable handle 20 in the direction indicated by arrow "A" (see FIG. 19), i.e., pivoted towards stationary handle 18, slide buttons 40 and 45 are movable from an upward position in which grasping pawl 60 is engaged in a slot 92b in toothed rack 92 of actuation shaft 90, to a downward position in which grasping pawl 60 is spaced from toothed rack 92 of actuation shaft 90. When grasping pawl 60 is positioned within slot 92b, only limited advancement and retraction of the actuation shaft 90 will occur upon operation of movable handle 20, allowing device 10 to operate in the grasping mode. In the upward position, protrusion 47 on slide button 45 is positioned within detent 108a. Downward movement of slide button 45 causes downward movement of protrusion 47 from detent 108a into detent 108b, as seen in FIG. 4. Reception of protrusion 47 within detents 108a and 108b provides the surgeon with an audible and/or tactile response to indicate a change in position/mode of slide buttons 40 and 45. During movement of movable handle 20 in the direction indicated by arrow "C" (see FIG. 21), i.e., movement towards its initial position that is spaced from stationary handle 18, a cam member 84 formed at the distal end of arm 80a slidably engages a camming surface 25 defined on a proximal side of movable handle 20 effecting clockwise rotation of yoke 80, such that arm 80b of yoke 80 engages a post 43 formed on the top end of slide button 45 to urge slide buttons 40 and 45 in the direction indicated by arrow "E" in FIG. 18 into the upward position. As shown in FIG. 23, grasping pawl 60 is moved downward by slot 92a in toothed rack 92 of actuation shaft 90.

Figure 24:
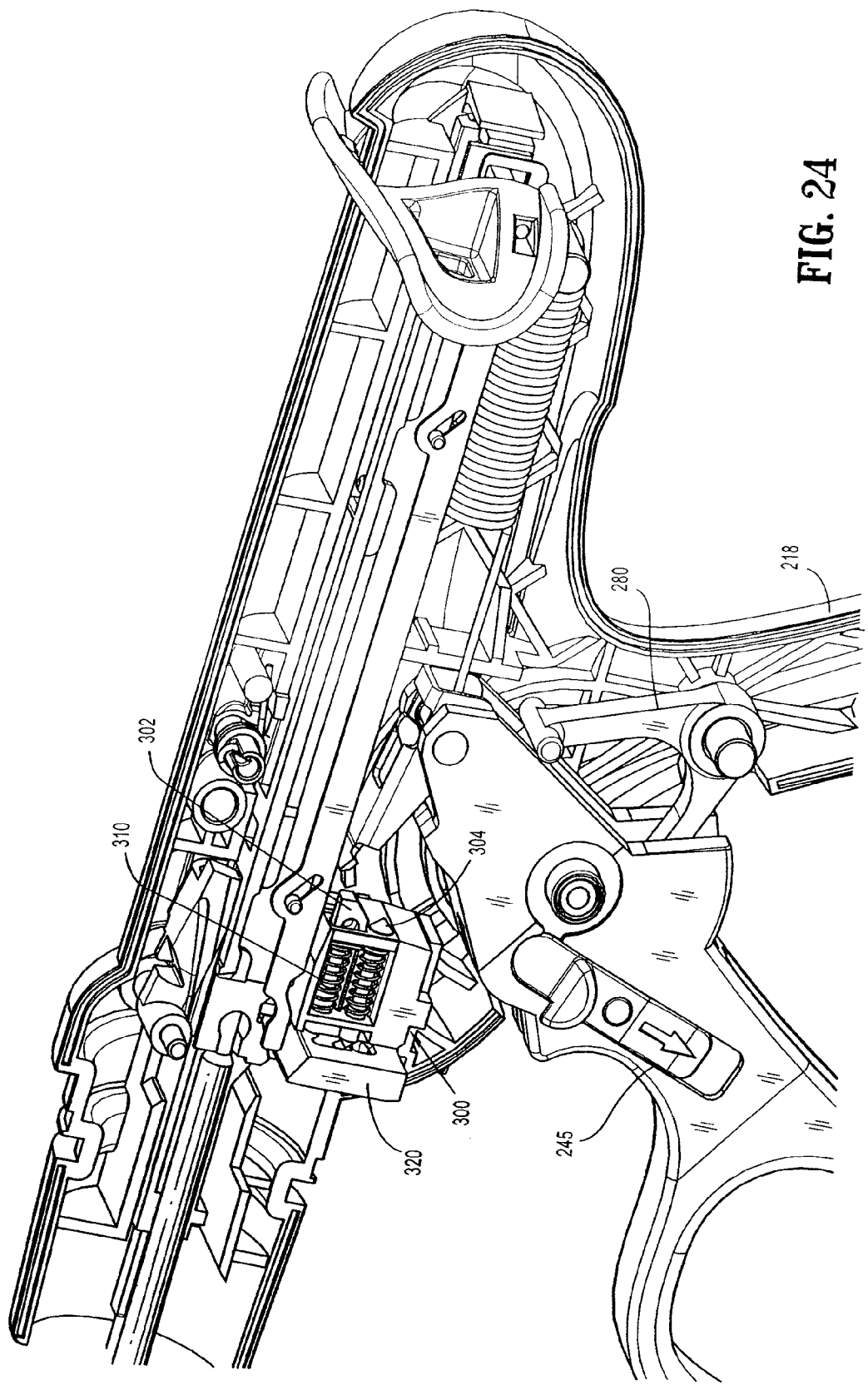
FIG. 24 is a side perspective of the handle assembly of the presently disclosed stapling device with a housing half-section removed and including an alternative embodiment of the grasping pawl assembly.
Figure 25:
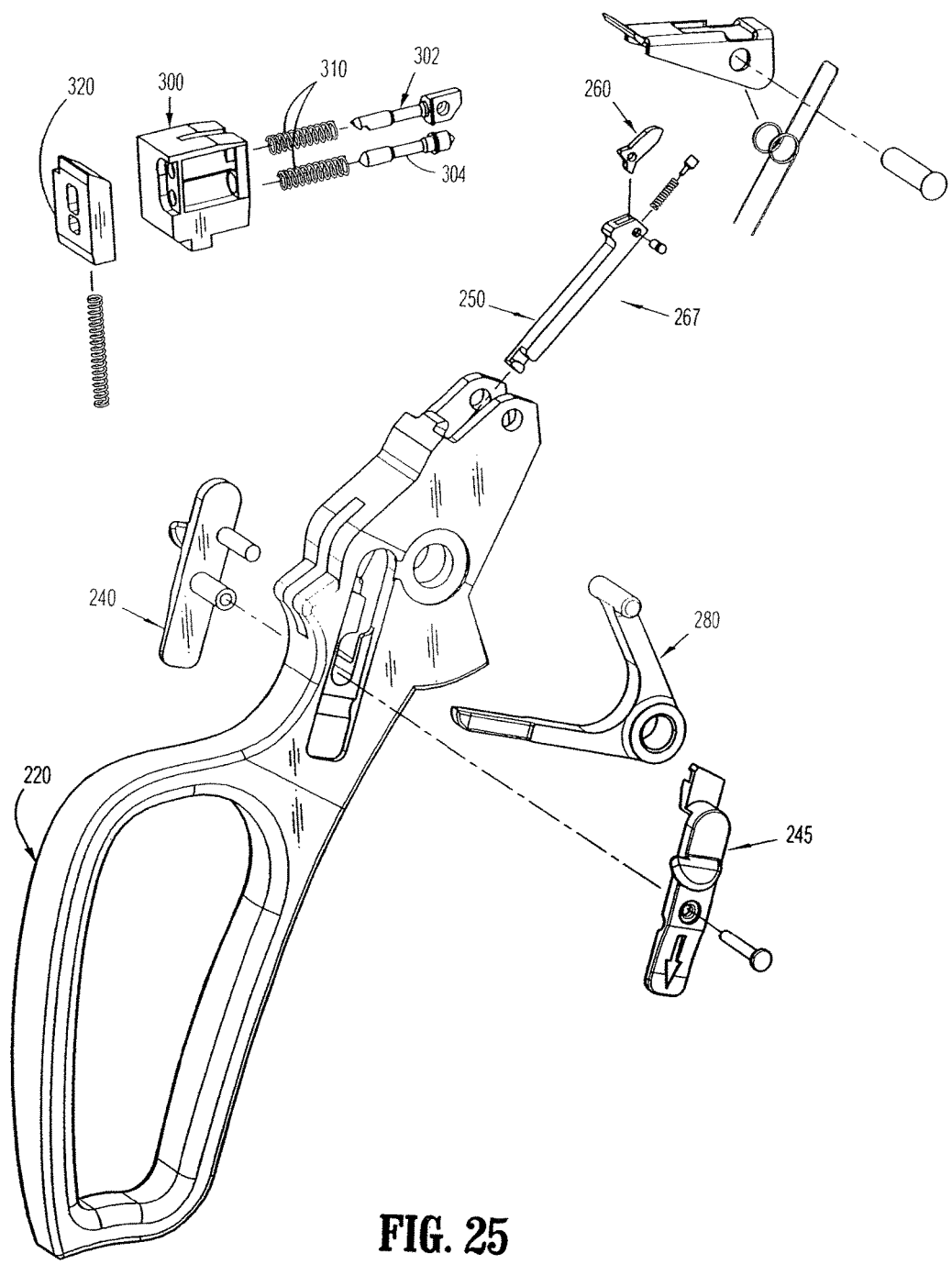
FIG. 25 is a side perspective view of the movable handle and grasping pawl assembly of the handle assembly shown in FIG. 24 with parts separated.

FIGS. 24-32 illustrate an alternative embodiment of the presently disclosed grasper pawl assembly shown generally as 267. Referring to FIGS. 24 and 25, grasper pawl assembly 267 is substantially as described above with respect to assembly 67 but includes additional features which will be discussed in detail below. As with assembly 67, grasper pawl assembly 267 includes a pawl arm 250, a grasper pawl 260, a yoke 280 and slide buttons 240 and 245. These elements function substantially as described above and will not be discussed in further detail herein.

Figure 26:
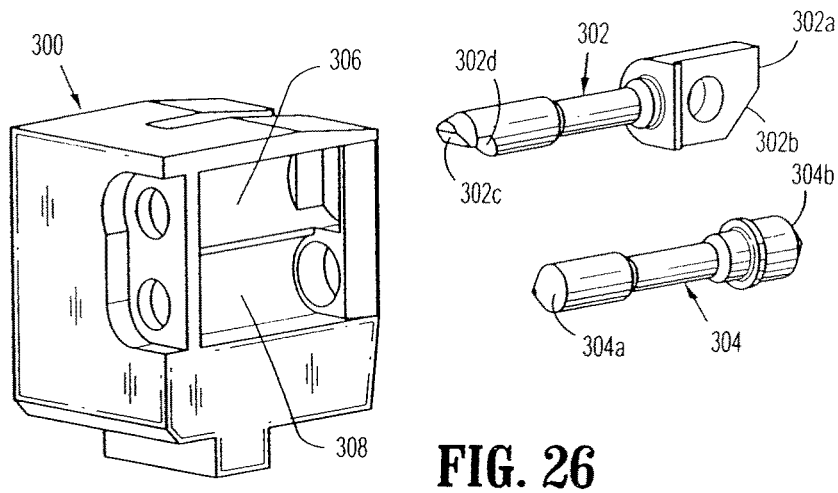
FIG. 26 is a perspective view from the distal end of the grasper adapter block assembly of the handle assembly shown in FIG. 24 with parts separated.
Figure 27:
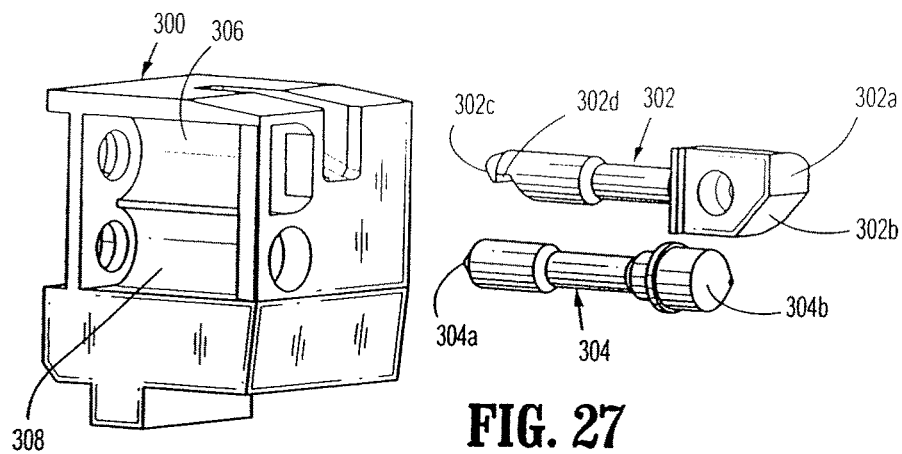
FIG. 27 is a perspective view from the proximal end of the adapter block assembly shown in FIG. 26.

Referring to FIGS. 25-27, grasper pawl assembly 267 further includes a grasper adapter block assembly including a grasper adapter block 300 which houses a pawl latch 302 and a disconnect member 304. Adapter block 300 includes a first recess 306 (FIG. 26) for slidably receiving pawl latch 302 and a second recess 308 for slidably receiving disconnect member 304. Each of pawl latch 302 and disconnect member 304 has length which is greater than the length of adapter block 300 such that the proximal and distal ends of latch 302 and member 304 extend from opposite ends of adapter block 300.

Pawl latch 302 has a proximal end 302a having an angled surface 302b and a tapered distal end 302c defining a catch member 302d. Disconnect member 304 includes tapered or rounded distal and proximal ends 304a and 304b. A biasing member or spring 310 is positioned in each of recesses 306 and 308 to urge pawl latch 302 and disconnect member 304 proximally.

Figure 28:
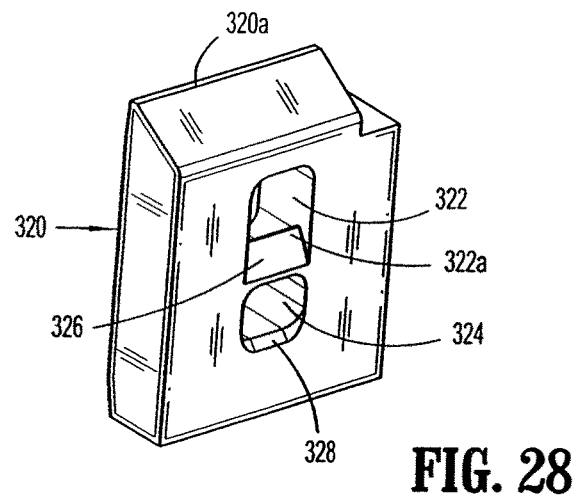
FIG. 28 is a perspective view of the vertical pawl of the handle assembly shown in FIG. 24.

Referring to FIG. 28, vertical pawl 320 includes a tip 320a and functions substantially as described above with respect to vertical pawl 120. Vertical pawl 320 includes an upper throughbore 322 and a lower throughbore 324. Upper throughbore 322 defines a stepped lip 322a which includes a tapered face 326. Lower throughbore 324 includes a tapered lower edge 328.

Adaptor block 300 is supported in handle assembly 213 such that the distal end of pawl latch 302 and disconnect member 304 are positioned adjacent vertical pawl 320. The proximal end of pawl latch 302 is positioned to engage sloped surface 255 of pawl arm 250 upon actuation of movable handle 220 when the pawl assembly 267 is in the grasper mode and pawl arm 250 is extended. When pawl assembly is retracted by moving slide buttons 240 and 245 (FIG. 25) downwardly on movable handle 220, the proximal surface of disconnect member 304 is positioned to engage sloped surface 255 of pawl arm 250 when movable handle 220 is actuated.

Figure 29:
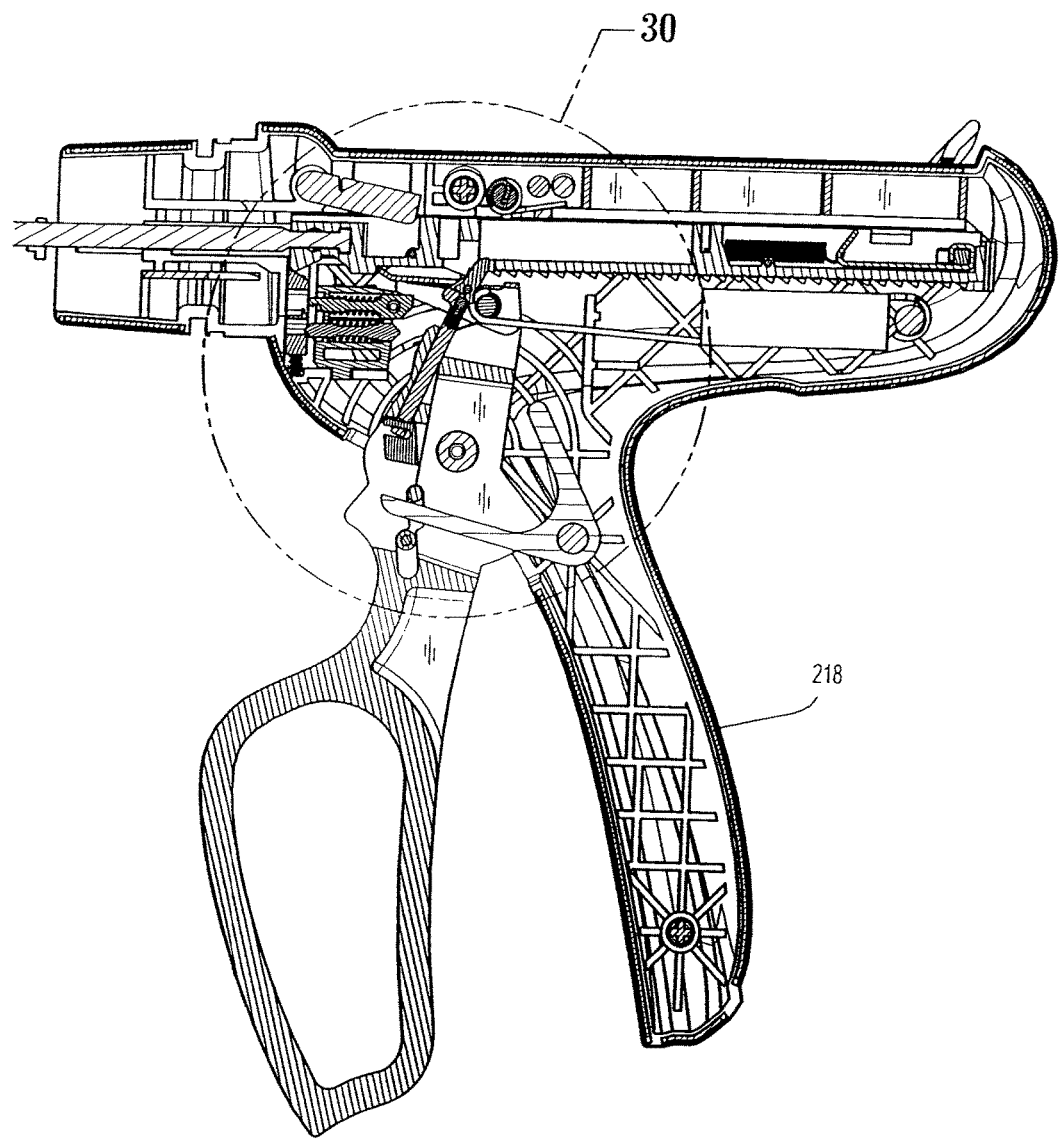
FIG. 29 is a side cross-sectional view of the handle assembly shown in FIG. 24 in the nest position.
Figure 30:
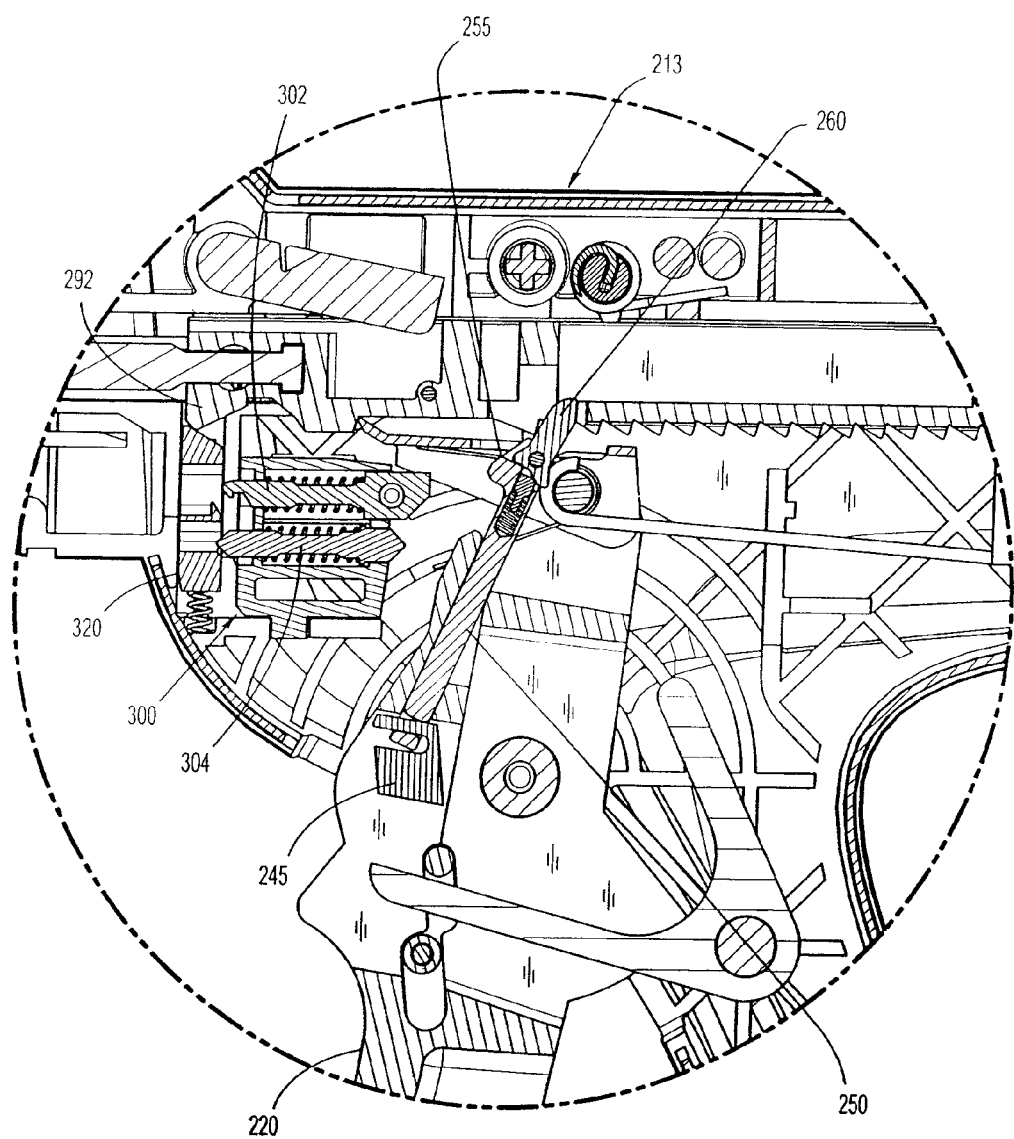
FIG. 30 is an enlarged view of the indicated area of detail shown in FIG. 29.

Referring to FIGS. 29 and 30, operation of adapter block 300 of pawl assembly 267 will now be described. When movable handle 220 is in its rest position spaced from stationary handle 218, pawl arm 250 is extended upwardly with sloped surface 255 spaced from the proximal ends of latch pawl 302 and disconnect member 304. Vertical pawl 320 is biased upwardly into engagement with the distal end of rack 292.

Figure 31:
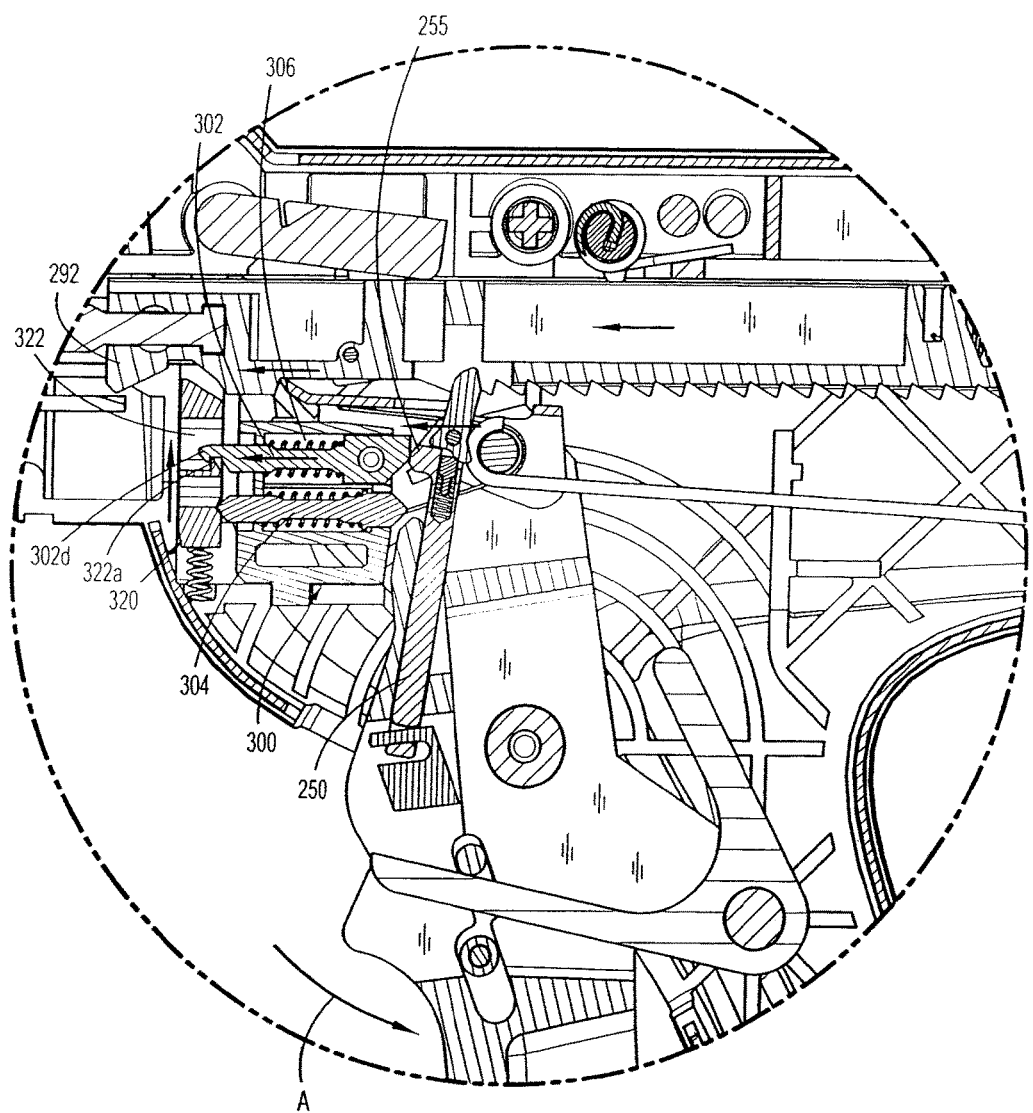
FIG. 31 is an enlarged view of the indicated area of detail shown in FIG. 29 with the movable handle actuated in the grasper mode.

Referring to FIG. 31, when movable handle 220 is moved in the direction indicated by arrow "A" towards stationary handle 218 (FIG. 24), sloped surface 255 of pawl arm 250 engages the proximal end of latch pawl 302 to advance latch pawl 302 distally along first recess 306 of adapter block 300 into upper throughbore 322 of vertical pawl 320. When this occurs, tapered distal end 302c (FIGS. 26 and 27) engages tapered face 326 of vertical pawl 320 to urge vertical pawl 320 downwardly out of engagement with rack 292. Catch member 302d receives stepped lip 322a of vertical pawl 320 to retain latch pawl 302 within upper throughbore 322 to lock vertical pawl 320 in a retracted position. Thus, vertical pawl 320 is prevented from engaging rack 292 and device 10 (FIG. 1) can be operated in grasper mode.

Figure 32:
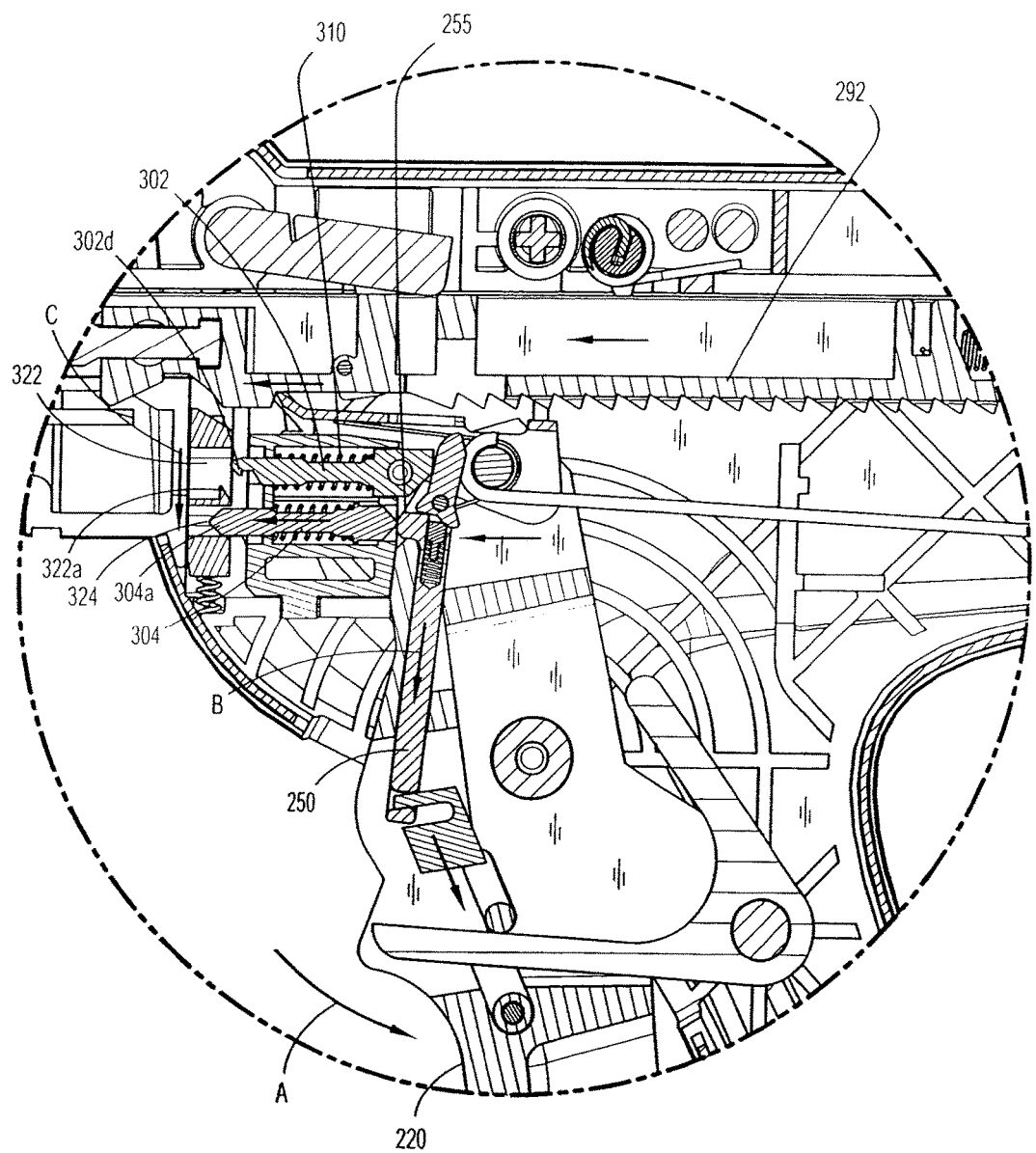
FIG. 32 is an enlarged view of the indicated area of detail shown in FIG. 29 with the movable handle actuated and the grasper mode deactivated.

Referring to FIG. 32, when pawl arm 250 is pulled downwardly, by moving slide buttons 240 and 245, in the direction indicated by arrow "B" and movable handle 220 is moved towards stationary handle 218 in the direction indicated by arrow "A", sloped surface 255 of pawl arm 250 engages proximal end 304b of disconnect member 304 and advances disconnect member 304 distally (See FIGS. 26 and 27). When this occurs, tapered distal end 304a of disconnect member 304 engages tapered lower edge 328 (FIGS. 26 and 27) of vertical pawl 320 and enters lower throughbore 324. Engagement between tapered distal end 304a of disconnect member 304 and tapered lower edge 328 of vertical pawl 320 urges vertical pawl 320 downwardly in the direction indicated by arrow "C" to disengage catch member 302d from stepped lip 322a. When this occurs, pawl latch 302 is moved by spring 310 to its retracted position spaced from vertical pawl 320. Thus, when movable handle 220 is returned to its rest position, disconnect member 304 is returned to its retracted position, spaced from vertical pawl 320, and vertical pawl 320 moves into engagement with rack 292 to prevent rack 292 from returning to its retracted position.

FIGS. 33-36A illustrate a surgical stapling device 400 including an alternative embodiment of the presently disclosed grasper jaw mechanism 500. Although not illustrated in FIGS. 33-36A, surgical stapling device 400 includes an elongated member which extends distally from a handle assembly 413, and a DLU which is releasably secured to a distal end of the elongated member. The elongated member and the DLU of stapling device 400 are substantially as described above with respect to elongated member 14 and DLU 16 of stapling device 10 (FIG. 1) and will not be described in further detail herein. Handle assembly 413 also includes a stationary handle 418 and a movable handle 420 which is rotatably supported between half-sections of handle assembly housing 412 as discussed above with respect to handle 20 of stapling device 10 (FIG. 1). A light spring or biasing member 422 (FIG. 33A) is provided to urge movable handle 420 away from stationary handle 418 from a compressed position (FIG. 33) to a non-compressed position (FIG. 34A). An advancement pawl 435 (FIG. 33) is pivotally supported about a pivot member 436 and urged towards a toothed rack 492 of an actuation shaft 490 by a biasing member 491. Actuation shaft 490 is substantially identical to actuation shaft 90 (FIG. 3) of surgical device 10 (FIG. 1) and will only be described in further detail as it relates to the description of grasper jaw mechanism 402. Handle assembly 413 also includes a vertical pawl 430 which is similar to vertical pawl 120 (FIG. 3) of stapling device 10. More specifically, vertical pawl 430 is urged upwardly by a biasing member 512 into engagement with a cutout 493 formed in a distal end of actuation shaft 490. When vertical pawl 430 is positioned within cutout 493 of actuation shaft 490, actuation shaft 490 is prevented from moving and the jaws of DLU 16 (FIG. 1) are prevented from opening.

Grasper jaw mechanism 500 includes a disconnect link assembly 502 and an actuator assembly 504. As will be discussed in further detail below, disconnect link assembly 502 functions to prevent engagement of vertical pawl 430 with actuation shaft 490 when handle assembly 413 is in grasper mode to allow for proximal and distal movement of actuation shaft 490. Actuator assembly 504 prevents the movable handle 420 from returning fully to the non-compressed position when handle assembly 413 is in grasper mode to prevent advancement pawl 435 from engaging toothed rack 492. By doing this, operation of movable handle 420 is prevented from advancing actuation shaft 490 distally beyond the clamped position of DLU 16 (FIG. 1) when handle assembly 413 is in grasper mode. Actuator assembly 504 also operatively connects movable handle 420 to actuation shaft 490 to allow a surgeon to unclamp the jaws of DLU 16 (FIG. 1) by manually moving movable handle 420 to the non-compressed position.

Figure 33:
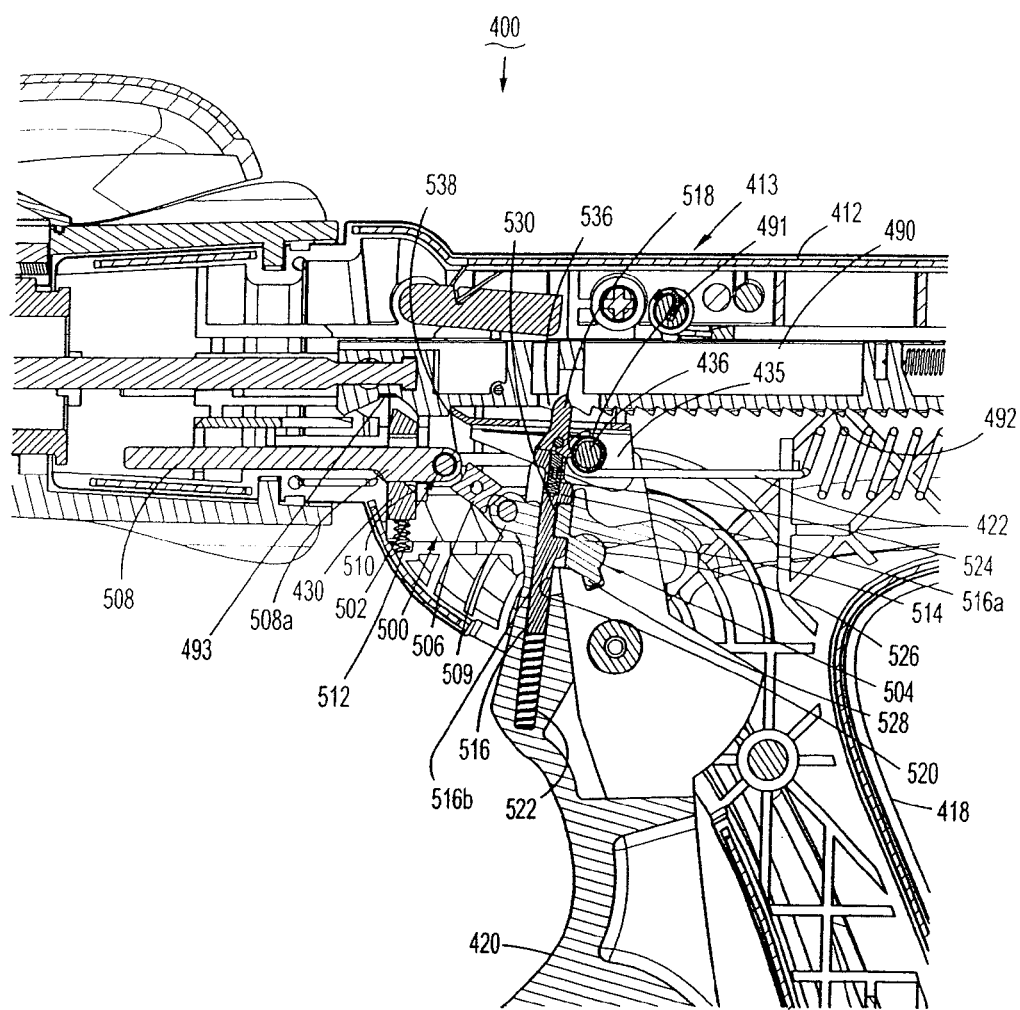
FIG. 33 is a side view of the handle assembly of the presently disclosed surgical stapling device with a housing half-section removed and including an alternative embodiment of a grasper jaw mechanism in grasper mode prior to advancement of the actuation shaft.
Figure 33A:
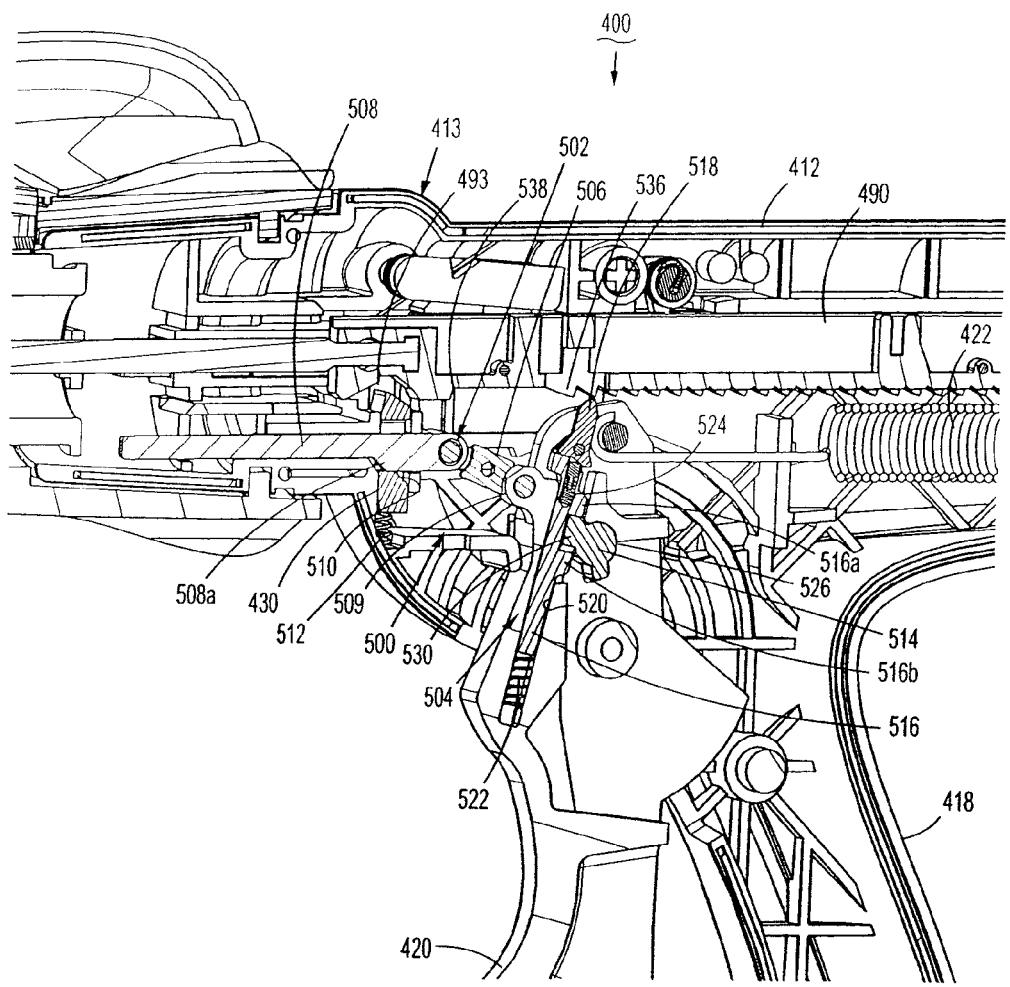
FIG. 33A is a side view of the handle assembly shown in FIG. 33 with the grasper jaw mechanism in a firing mode and the movable handle partially compressed.
Figure 34:
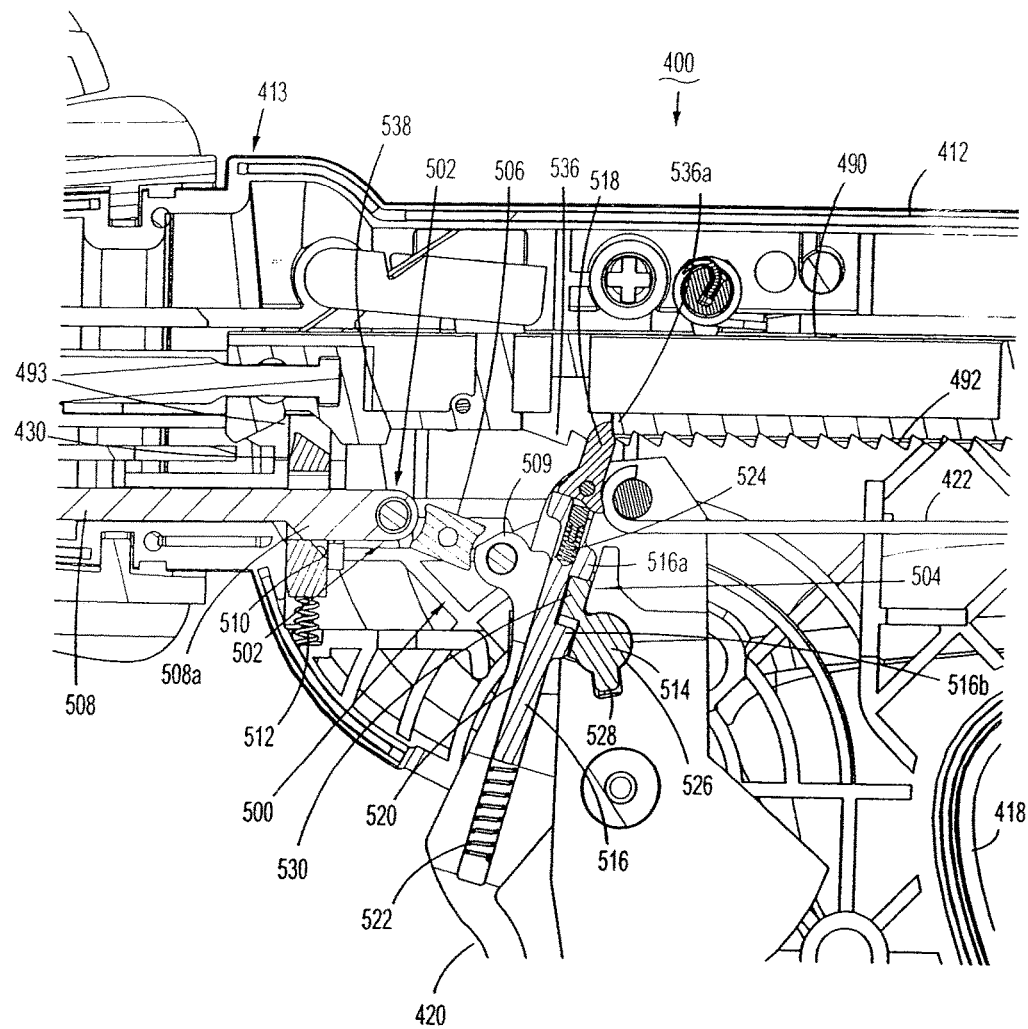
FIG. 34 is a side view of the handle assembly shown in FIG. 33 with the grasper jaw mechanism in grasper mode and the actuation shaft advanced to move a DLU to a clamped position.
Figure 34A:
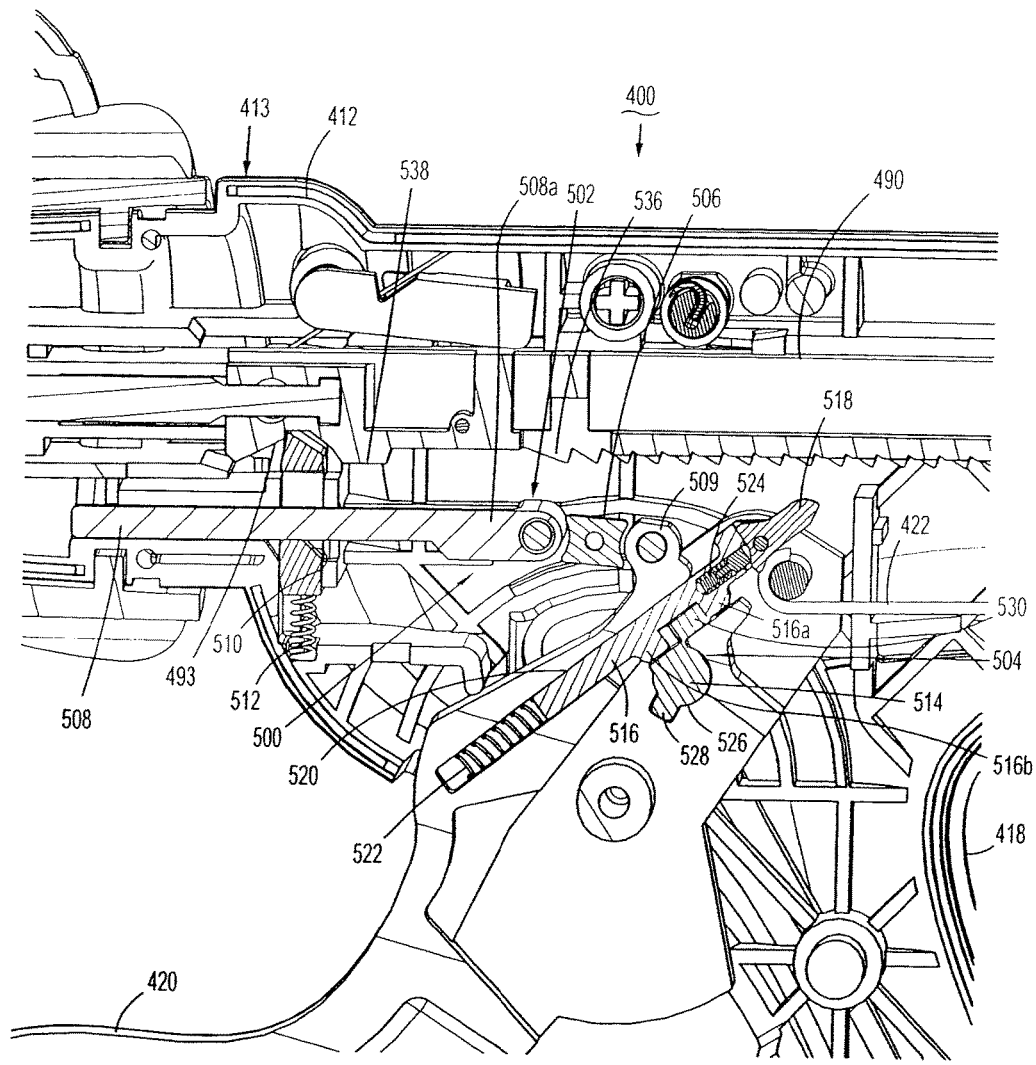
FIG. 34A is a side view of the handle assembly shown in FIG. 3A with the grasper jaw mechanism in firing mode and the movable handle in a non-compressed position.
Figure 34B:
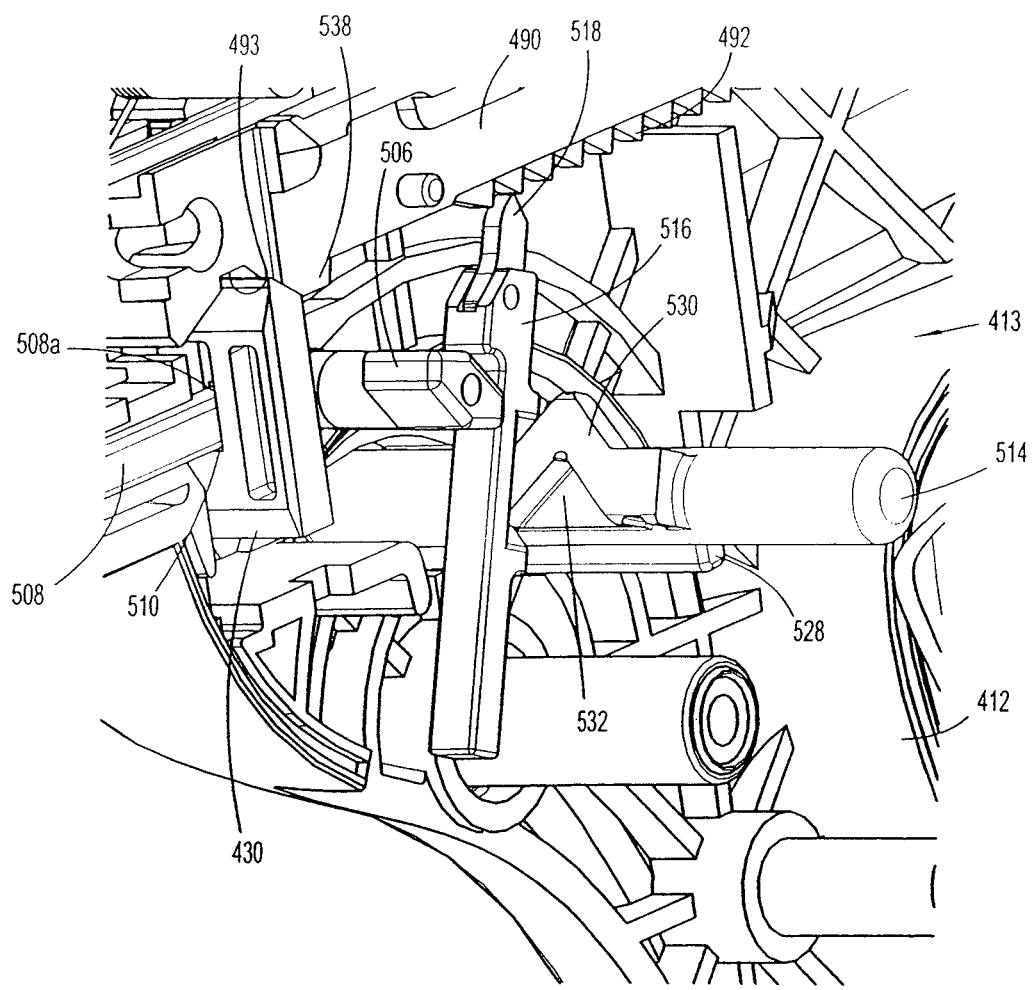
FIG. 34B is an enlarged, side perspective view of a portion of the handle assembly shown in FIG. 34A illustrating the grasper jaw mechanism in firing mode.

Referring to FIGS. 33-34B, disconnect link assembly 502 includes a proximal link 506 and a distal link 508. Proximal link 506 has a proximal end pivotally secured to a cylindrical boss 509 (FIGS. 33-34A) formed on movable handle 420 and a distal end pivotally secured to a proximal end of distal link 508. Distal link 508 is linearly slidable along a track defined within housing 412 of handle assembly 413 and includes an angled stepped portion 508a formed at its proximal end. Distal link 508 is slidably positioned to engage a cam surface 510 formed on or through vertical pawl 430. As discussed above, vertical pawl 430 is urged upwardly by a biasing member 512 into engagement with a cutout 493 formed in actuation shaft 490 to prevent movement of actuation shaft 490 after DLU 16 (FIG. 1) has been moved to a clamped position. When stepped portion 508a of distal link 508 is moved distally into engagement with cam surface 510 of vertical pawl 430 by moving movable handle 420 towards stationary handle 418, vertical pawl 430 is moved downwardly against the bias of biasing member 512 out of engagement with actuation shaft 490. When this occurs, actuation shaft 490 is free to move proximally as will be discussed in further detail below.

Figure 35:
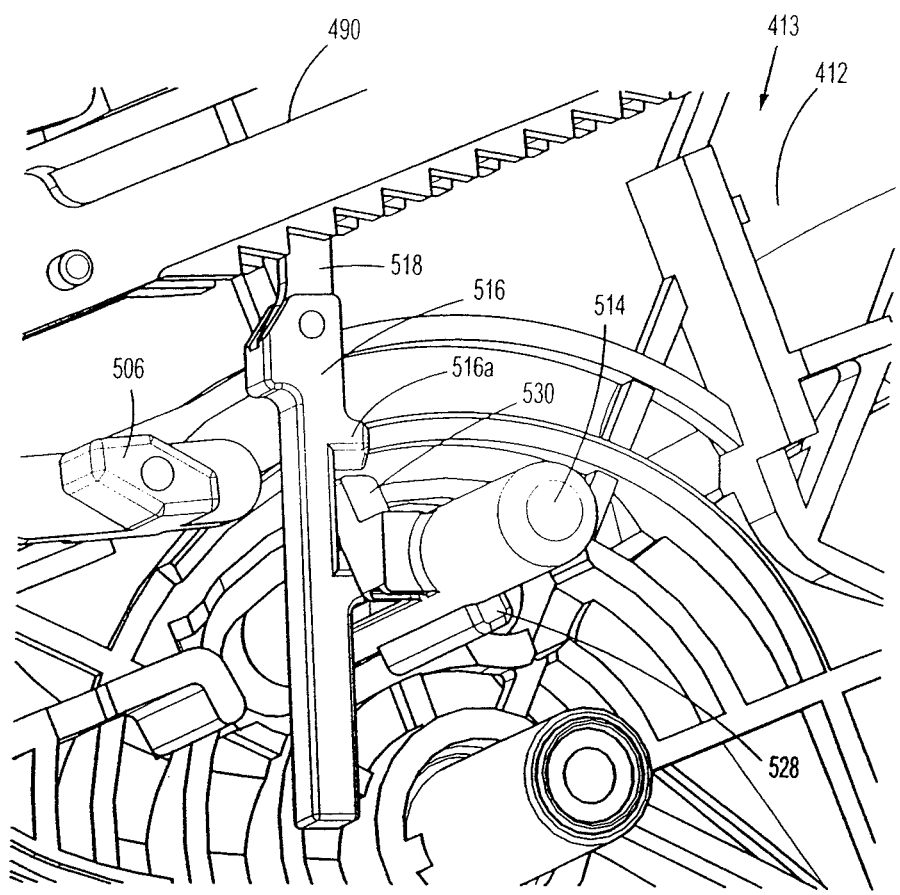
FIG. 35 is an enlarged side perspective view of a portion of the handle assembly shown in FIG. 34 illustrating the actuator assembly of the grasper jaw mechanism in grasper mode.
Figure 36:
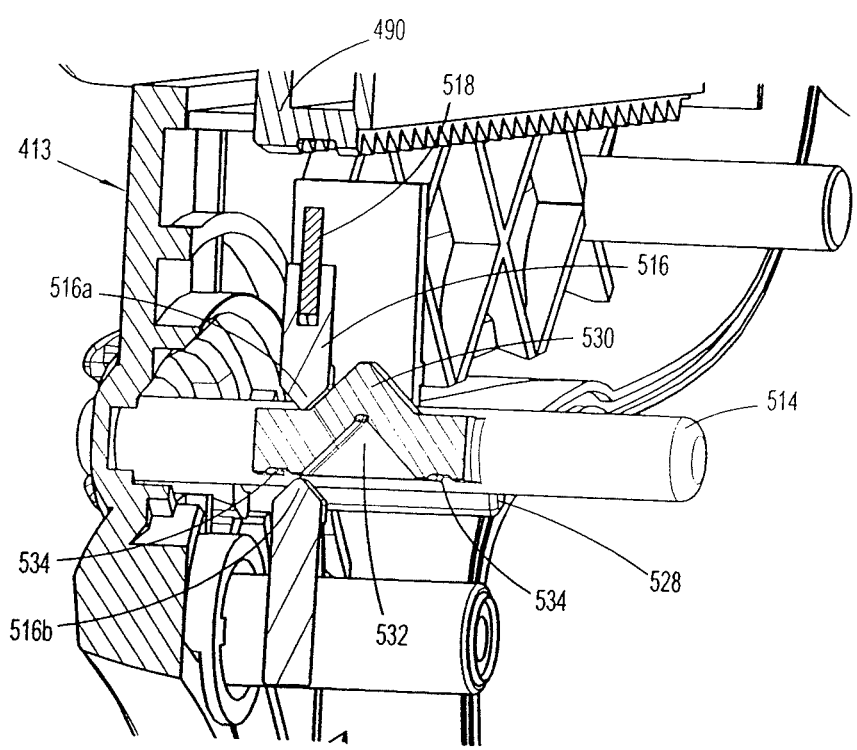
FIG. 36 is an enlarged side perspective view of a portion of the handle assembly shown in FIG. 34A illustrating the actuator assembly of the grasper jaw mechanism in firing mode.
Figure 36A:
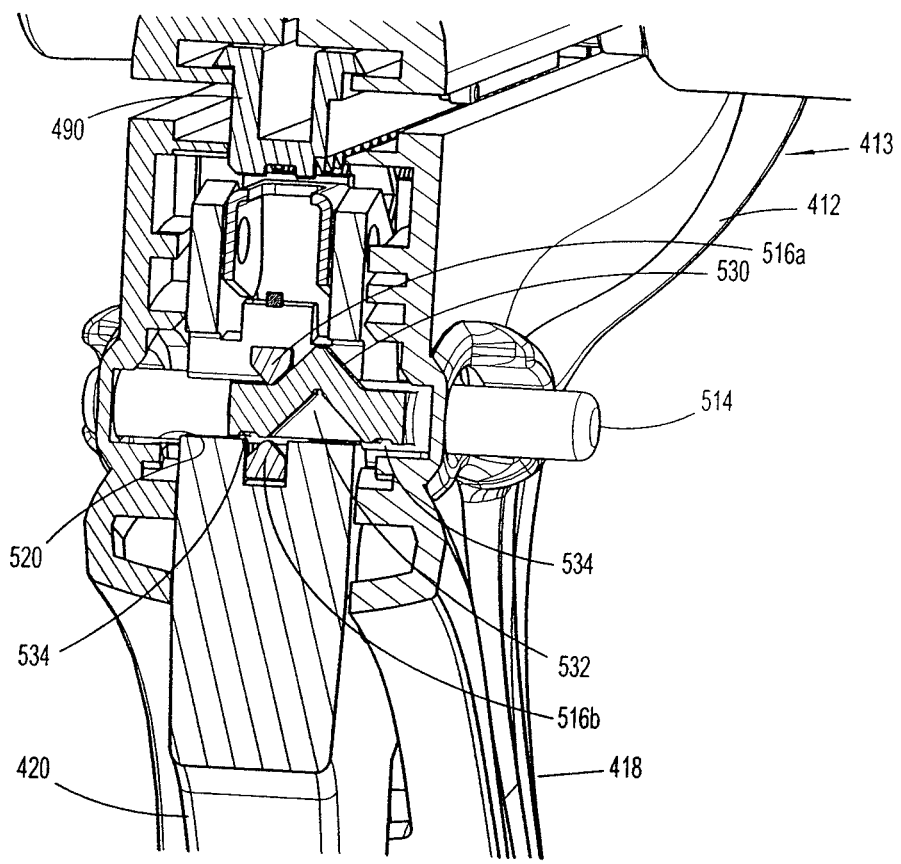
FIG. 36A is a front cutaway view of a portion of the handle assembly shown in FIG. 34A illustrating the actuator assembly of the grasper jaw mechanism in firing mode.

Referring also to FIGS. 35-36A, actuator assembly 504 includes an actuator button 514 and, a slider or other engagement member such as a pawl arm 516 and a grasping pawl 518. Pawl arm 516 is slidably received in a recess 520 formed in movable handle 420. A biasing member 522, e.g., a coil spring, is positioned within recess 520 (FIG. 33A) to urge pawl arm 516 towards an extended position. Pawl arm 516 has upper and lower spaced triangular cam surfaces 516a and 516b which will be discussed in further detail below. Grasping pawl 518 is pivotally supported within a slot formed in a distal end of pawl arm 516. A biasing member 524 is positioned to urge grasping pawl 518 in a counter-clockwise direction as viewed in FIG. 33. Pivoting movement of grasping pawl 518 allows pawl arm 518 to ratchet or slide over toothed rack 492 of actuation shaft 490.

Figure 35A:
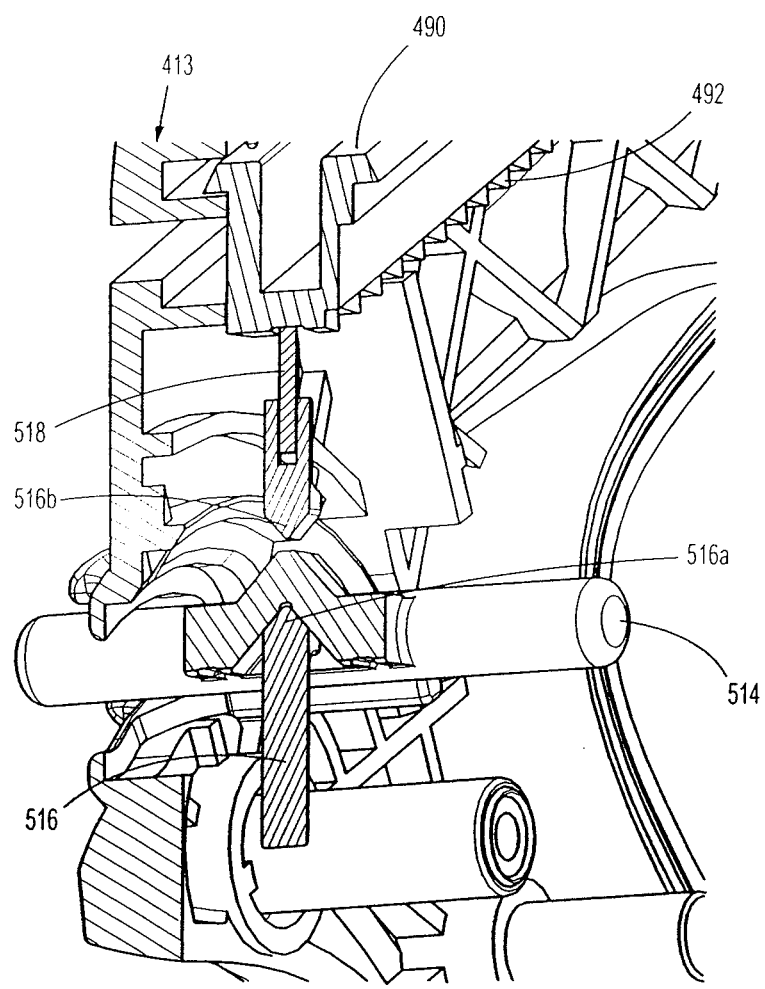
FIG. 35A is a front cutaway view of a portion of the handle assembly shown in FIG. 35 illustrating the actuator assembly of the grasper jaw mechanism in grasper mode.

Actuator button 514 is slidably positioned through a bore 526 (FIG. 35C) formed in movable handle 420 from a centered position (FIGS. 35-35C) to an off-center position (FIGS. 36-36A). Bore 526 is substantially orthogonal to recess 520 such that actuator button 514 is slidably positioned between upper and lower cam surfaces 516a and 516b of pawl arm 516. In one embodiment, actuator button 514 is substantially cylindrical and includes a linear rib 528 and a v-shaped cam member 530. V-shaped cam member 530 defines a slot 532 (FIG. 36) which is configured to receive lower cam surface 516b of pawl arm 516 when actuator button 514 is in the centered position and pawl arm 516 is in a extended position with recess 520. Actuator button 514 defines recesses 534 (FIG. 36) on opposite sides of slot 532. Opposite ends of actuator button 514 extend from opposite sides of housing 412 of handle assembly 413 and can be pressed by a surgeon from either side of handle assembly 413 to move actuator button 514 linearly through bore 526 in either direction to move actuator button 514 from the centered position to the off-center position. When actuator button 514 is moved linearly within bore 526, lower cam surface 516b is engaged by v-shaped cam member 530 to urge pawl arm 516 from its initial, extended position, downwardly within recess 520 to its retracted position. When actuator button 514 is moved linearly to its off-center position and pawl arm 516 is cammed to its retracted position, the apex of lower cam surface 516b is received within one of recesses 534 to retain actuator button 514 in its actuated position. See FIGS. 36-36A. When pawl arm 516 is moved to the retracted position, grasping pawl 518 is also moved from an initial extended position, to a retracted position and is withdrawn from slot 536 of actuation shaft 490.

In its initial or original position shown in FIG. 33, actuator button 514 is in its centered position and pawl arm 516 is urged to its extended position by biasing member 522. When pawl arm 516 is in its extended position, grasping pawl 518 is positioned to extend into a slot 536 (FIG. 35A) formed in actuation shaft 490. When movable handle 420 is actuated, advancement pawl 435 engages an abutment 538 on actuation shaft 490 (FIG. 33) to advance the actuation shaft 490 distally to move DLU 16 to a clamped position as discussed above. As movable handle 420 is compressed towards stationary handle 418, distal link 508 is also moved distally such that stepped portion 508a of distal link 508 engages cam surface 510 of vertical pawl 430 to urge vertical pawl 430 downwardly against the bias of spring 512 away from actuation shaft 490. When movable handle 420 is returned to its non-compressed position by spring 422, grasping pawl 518 engages the proximal portion 536a (FIG. 34) of actuation shaft 490 defining slot 536 to retain movable handle in an intermediate position between the non-compressed and compressed positions. It is noted that spring 422 is a light spring which cannot move actuation shaft 490 proximally because of friction associated with the components of DLU 16 (FIG. 11 driven by actuation shaft 490. However, a surgeon can manipulate movable handle 420 to move actuation shaft 490 and, thus, move DLU 16 (FIG. 1) between an unclamped position and a clamped position. Because vertical pawl 430 is retained in its retracted position by distal link 508, actuation shaft 490 is permitted to move proximally. It is noted that movable handle 420 is prevented from moving to the non-compressed position by engagement of grasping pawl 518 with proximal portion 536a of slot 536. This prevents movable handle 420 from retracting distal link 508 to a position to disengage stepped portion 508a of distal link 508 from vertical pawl 430. Thus, vertical pawl 430 remains disengaged from actuation shaft 490.

Referring to FIGS. 33A, 34A and 36-36A, when movable handle 420 is moved to the compressed position and actuator button 514 is moved from the centered position to the off-center position, v-shaped cam member 530 engages cant surface 510 on pawl arm 516 to retract pawl arm 516 within recess 520 (FIG. 33A) of movable handle 420 and retract grasping pawl 518 from within slot 536 of actuation shaft 490. When grasping pawl 518 is removed from slot 536, biasing member 422 returns movable handle 420 to its non-compressed position (FIG. 34A). When this occurs, distal link 508 is pulled proximally by movable handle 420, disengaging stepped portion 508a of distal link 508 from cam surface 510 of vertical pawl 430. Vertical pawl 430 is moved by biasing member 512 into engagement with cutout 493 in actuation shaft 490 to prevent proximal movement of actuation shaft 490. Thus, when movable handle 420 is again moved to the compressed position, advancement pawl 435 (FIG. 33) engages toothed rack 492 of actuation shaft 490 to fire DLU 16 (FIG. 1) in the manner discussed above with respect to surgical device 10. As actuation shaft 490 is moved distally, vertical pawl 430 ratchets or slides over toothed rack 492 of shaft 490.

Figure 35B:
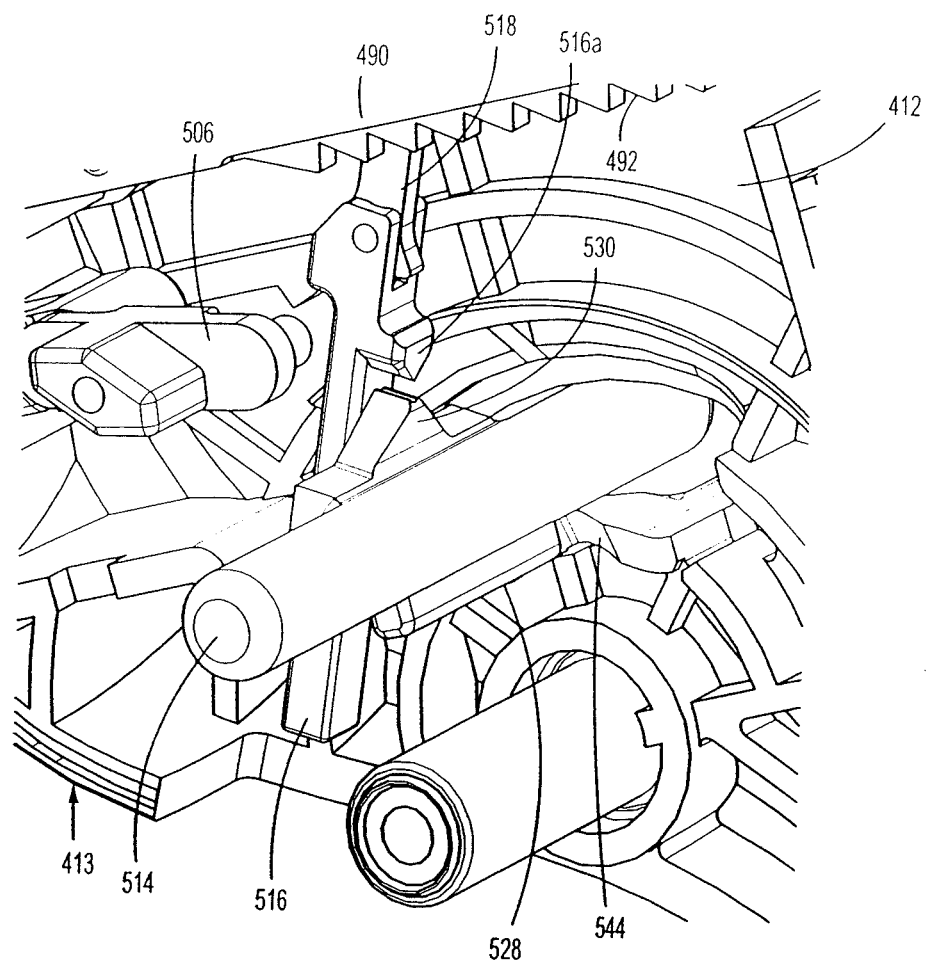
FIG. 35B is another enlarged side perspective view of a portion of the handle assembly shown in FIG. 34 illustrating the actuator assembly of the grasper jaw mechanism in grasper mode.
Figure 35C:
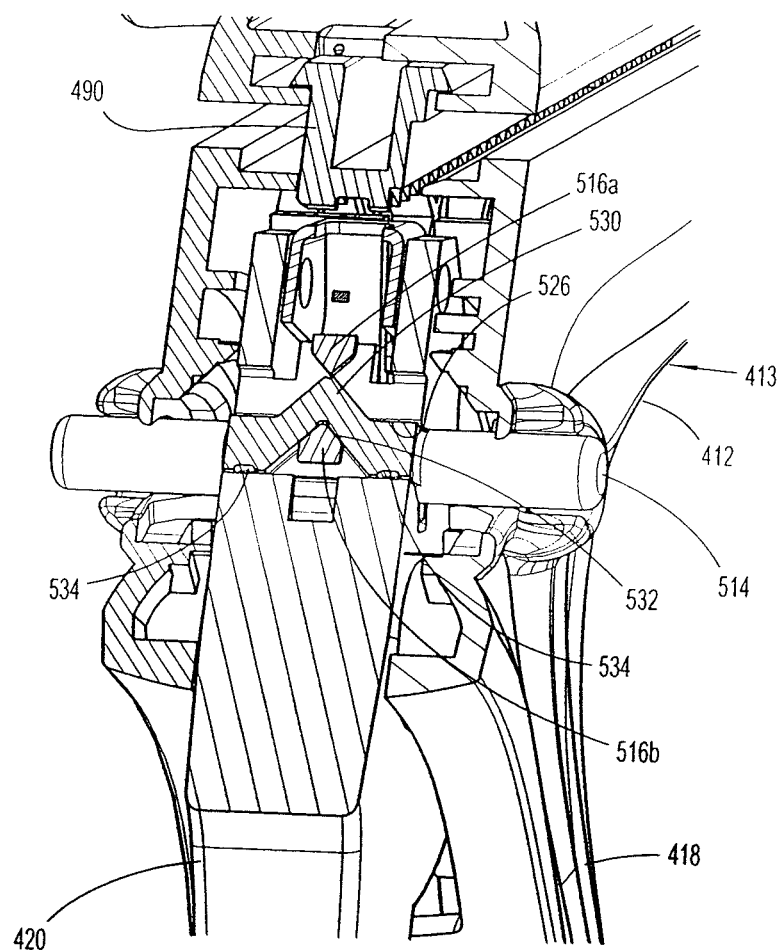
FIG. 35C is another front cutaway view of a portion of the handle assembly shown in FIG. 35 illustrating the actuator assembly of the grasper jaw mechanism in grasper mode.

As illustrated in FIG. 35B, in one embodiment, when actuator button 514 has been actuated and is in its off-center position, linear rib 528 is moved to a position to engage a cam surface 544 positioned on an inner wall of housing 412. Cam surface 544 includes an angled face which is positioned to engage linear rib 528 when movable handle 420 returns to its non-compressed position to return actuator button 514 to its centered position.

As discussed above, actuator button 514 is supported on movable handle 420 and extends through opposite sides of housing 412 of handle assembly 413. In order to facilitate, movement of actuator button 514 with movable handle 420, arc shaped slots (not shown) are provided in housing 412. In one embodiment, raised surfaces or bosses are provided about a portion of the arc shaped slots which prevent depressing actuator button 514 until movable handle 420 has been moved to a compressed position. As discussed above, the grasping pawl 518 is pivotably supported at a distal end of pawl arm 516. In other embodiments, the assembly is dimensioned so that the actuator button 514 moves the pawl arm 516 away from the teeth of the actuation shaft. As discussed above, the surgical device is initially in the grasper mode, with the grasping pawl 518 in engagement with the actuation shaft and the actuator button 514 moves the grasping pawl 518 into a position in which the grasping pawl 518 no longer moves the actuation shaft as the movable handle 420 is pivoted. In other embodiments, the surgical device is initially in an alternate mode, with the grasping pawl 518 in a position in which the grasping pawl 518 does not move the actuation shaft as the movable handle 420 is pivoted. When the actuator button is pushed, the grasping pawl is moved into a position in which the grasping pawl 518 moves the actuation shaft as the movable handle 420 is pivoted.

In each embodiment discussed above, retractor knobs are manually grasped to retract the actuation shaft. For example, a retraction mechanism which includes retractor knobs 15 (see FIG. 1) is connected to the proximal end of actuation shaft 90 by a coupling rod 96. Coupling rod 96 includes left and right engagement portions 96a and 96b which extend through elongated slots 17 formed in housing half-sections 12a and 12b and are configured to receive retractor knobs 15. A central portion of 96c of coupling rod 96 is dimensioned and configured to be slidably received within a pair of opposed slots 98 formed in actuation shaft 90 adjacent the proximal end thereof. A release plate 70 is supported on one side of actuation shaft 90 by a pair of spaced apart pins 91 (see FIG. 3). Pins 91 extend outwardly from a lateral face of actuation shaft 90 to engage a pair of angled cam slots 71 formed through release plate 70. In this way, release plate 70 is operatively associated with actuation shaft 90 and is mounted for movement with respect thereto in response to manipulation of retractor knobs 15.

In use, when retractor knobs 15 are pulled rearwardly or proximally, coupling rod 96 initially moves release plate 70 rearward in relation to actuation shaft 90 as coupling rod 96 slides in slots 98 of actuation shaft 90. As this occurs, release plate 70 is moved downwardly by pins 91 with respect to actuation shaft 90 thereby covering toothed rack 92 to disengage engaging finger 35a of advancement pawl 35 from toothed rack 92. Once coupling rod 96 reaches a position at which it engages the proximal end of slots 98, additional rearward movement of retractor knobs 15 causes retraction of actuation shaft 90 and thus retraction of control rod 95 rearwardly. Actuation shaft 90 is biased proximally by spring 64 which is secured at one end to coupling rod portion 96c via a connector 75 and at the other end to a post 77 on actuation shaft 90.

Figure 19:
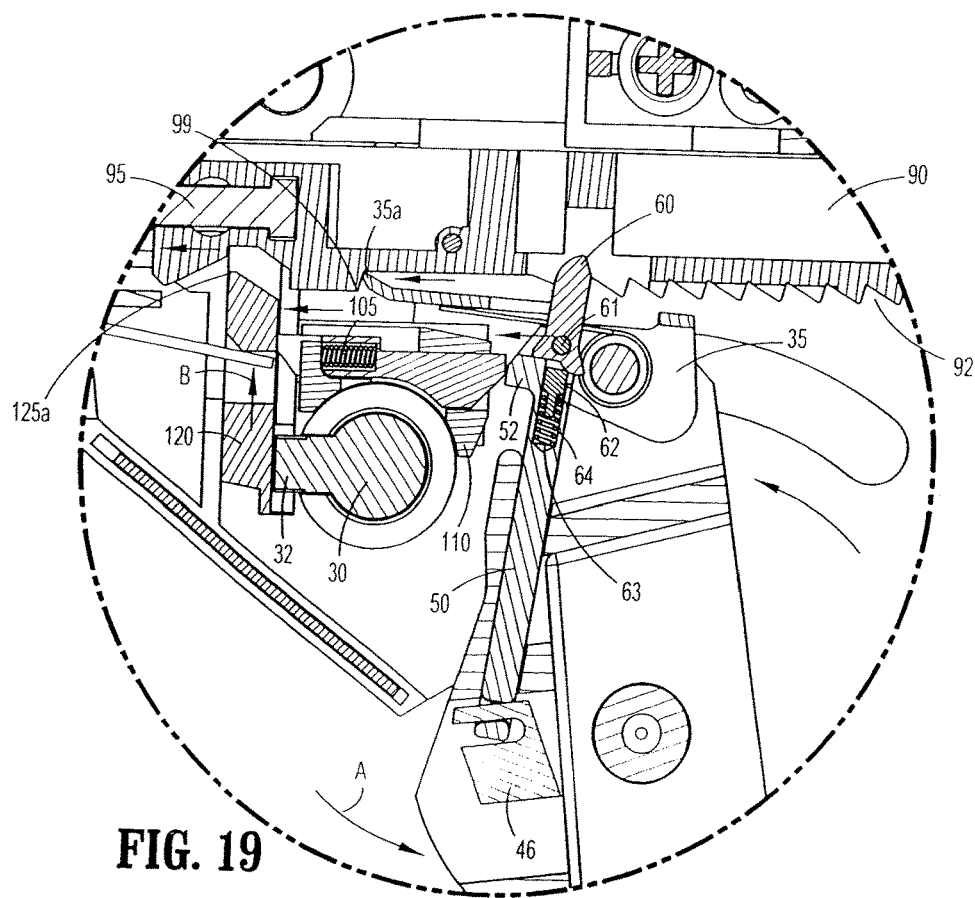
FIG. 19 is a side cross-sectional view, illustrating the movable handle pivoted towards the stationary handle.

In certain embodiments discussed above, the surgical stapling device is initially in the grasping mode. For example, surgical stapling device 10 is initially in the grasping mode. Referring to FIG. 19, movable handle 20 is manipulated to open and approximate cartridge assembly 26 and anvil assembly 28, back and forth, in a reciprocal fashion. Movable handle 20 is moved in the direction indicated by arrow "A" through a grasping stroke, wherein movable handle 20 is pivoted towards stationary handle 18 against the bias of a torsion spring (not shown) to move engagement finger 35a of advancement pawl 35 into engagement with a shoulder 99 formed on actuation shaft 90. Subsequent movement of movable handle 20 through the grasping stroke rotates pawl arm 50 counter-clockwise. Counter-clockwise rotation of pawl arm 50 causes sloped surface 55 of outturned portion 52 of pawl arm 50 to engage proximal surface 100a of cam member 100, biasing cam member 100 into the extended or distal position. In the extended or distal position, tip 102 of cam member 100 engages tip 125 of vertical pawl 120 to retain vertical pawl 120 in the retracted position (see FIG. 20). In the retracted position, vertical pawl 120 is spaced from actuation shaft 90, allowing actuation shaft 90 to return to the retracted position upon subsequent movement of movable handle 20 in the direction indicated by arrow "C".

Figure 21:
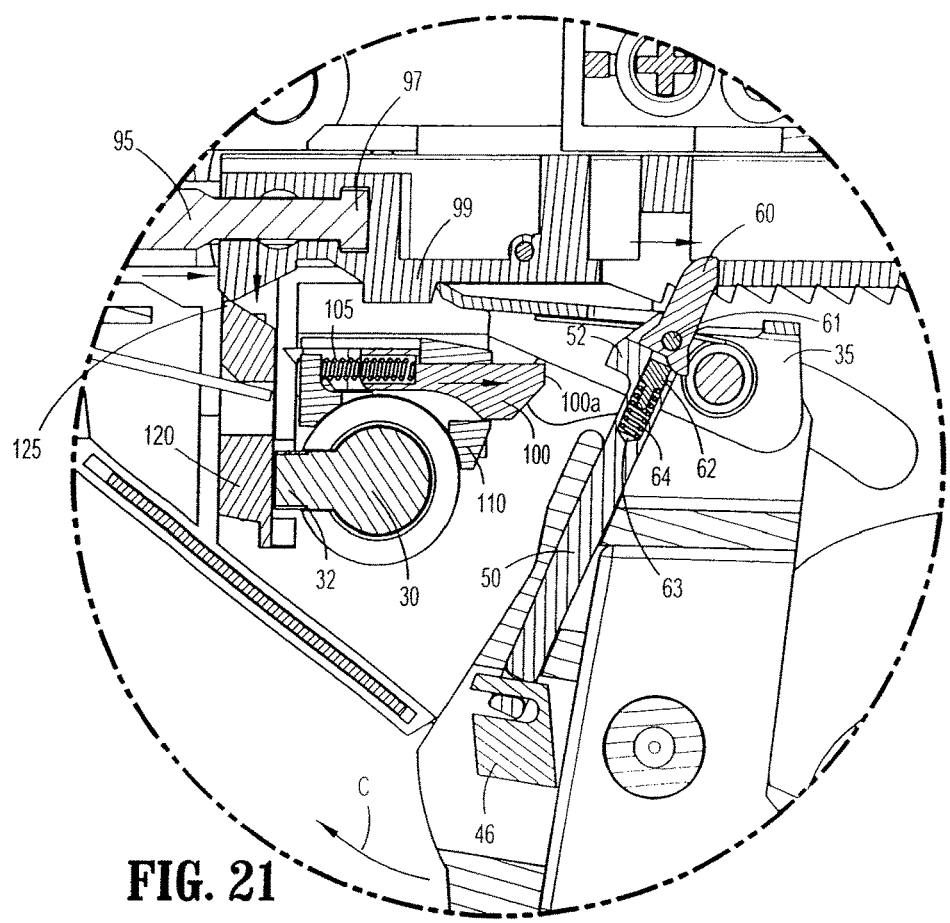
FIG. 21 is a side cross-sectional view, illustrating the movable handle biased away from the stationary handle.
Figure 22:
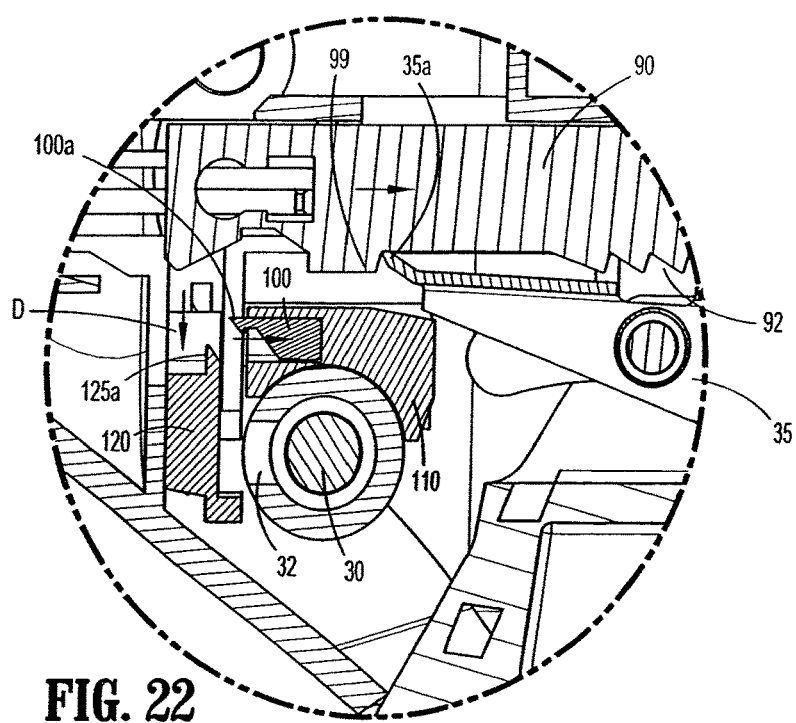
FIG. 22 is a side cross-sectional view, illustrating the actuation shaft in the retracted position.

Referring to FIG. 21, after movable handle 20 has been actuated to approximate cartridge and anvil assemblies 26 and 28, and movable handle 20 is released by the user, a biasing member (not shown) returns movable handle 20 in the direction indicated by arrow "C" to its initial position. As movable handle 20 returns to its initial position, arm 80b of yoke 80 slides slide buttons 40, 45 upwardly, so that device 10 remains in gasping mode. Sliding slide buttons 40, 45 downwardly changes the mode of device 10 to the clamping mode, so that subsequent movement of movable handle 20 in the direction "A" clamps cartridge assembly 26 and anvil assembly 28 onto tissue. Vertical pawl 120 moves into engagement with cutout 93 in actuation shaft 90 to lock actuation shaft 90 in position. When plunger 30 is pressed inward towards housing half-sections 12a and 12b, cam member 32 of plunger 30 engages cam surfaces 122 of vertical pawl 120 such that cam member 32 is releasably received in recesses 124 to urge vertical pawl 120 in the direction indicated by arrow "D" in FIG. 22 to its retracted position. In the retracted position, tip 125 of vertical pawl 120 is outside of cutout 93 in actuation shaft 90 and device 10 is in the grasping-ready mode. Vertical pawl 120 is maintained in the retracted position by engagement between cam member 32 of plunger 30 and recesses 124 on cam surfaces 122 of vertical pawl 120. In this position, vertical pawl 120 is in the extended position with tip 125 of vertical pawl 120 positioned within cutout 93 in actuation shaft 90, thus preventing further advancement of actuation shaft 90. In the extended position, cam member 32 of plunger 30 is aligned between cam surfaces 122 of vertical pawl 120.

Movable handle 20 returns to its initial position and urges yoke 80 to rotate clockwise. Clockwise rotation of yoke 80 forces arm 80b of yoke 80 to engage post 43 on slide button 45 to urge slide buttons 40 and 45 into the upward position. In the upward position, grasping pawl 60 is pivotally biased downward by slot 92a in toothed rack 92, instead of slot 92b, as toothed rack 92 has been advanced (see FIG. 23). Device 10 is now in a fire-ready mode. Movable handle 20 is moved in the direction indicated by arrow "A" in FIG. 19 through a second, firing stroke, during which advancement pawl 35 engages toothed rack 92 of actuation shaft 90 to advance actuation shaft 90 and control rod 95 distally. Referring again to FIG. 19, as actuation shaft 90 moves distally, shoulder 99 formed on actuation shaft 90 engages vertical pawl 120 to move vertical pawl 120 downwardly to disengage cam member 32 of plunger 30 from cam surfaces 122 of vertical pawl 120 and allow spring (not shown) to return plunger 30 to the neutral position, i.e., in a non-compressed position. Subsequent motion of movable handle 20 in the direction indicated by arrow "C" in FIG. 21 further advances toothed rack 92. Retractor knobs 15 are used to retract actuation shaft 90 and thus control rod 95 rearwardly, realigning grasping pawl 60 within slot 92b of toothed rack 92. Device 10 is now returned to the grasping-ready mode.

Often in endoscopic procedures, tissue must be manipulated or pulled aside to allow surgeons to access and/or view the tissue site before clamping and stapling can be performed. Selectable modes of operation appreciated by the present disclosure allows surgeons the benefit of operating device 10 in the grasping mode wherein tool assembly 27 may be manipulated by operation of movable handle 20 to grasp and manipulate tissue before easily switching device 10 to the clamping mode of operation wherein tool assembly 27 is configured to clamp tissue and apply staples. The mechanisms discussed above may be used to change between modes, in surgical devices other than stapling devices. DLUs other than a stapling DLU may be used.

Figure 14:
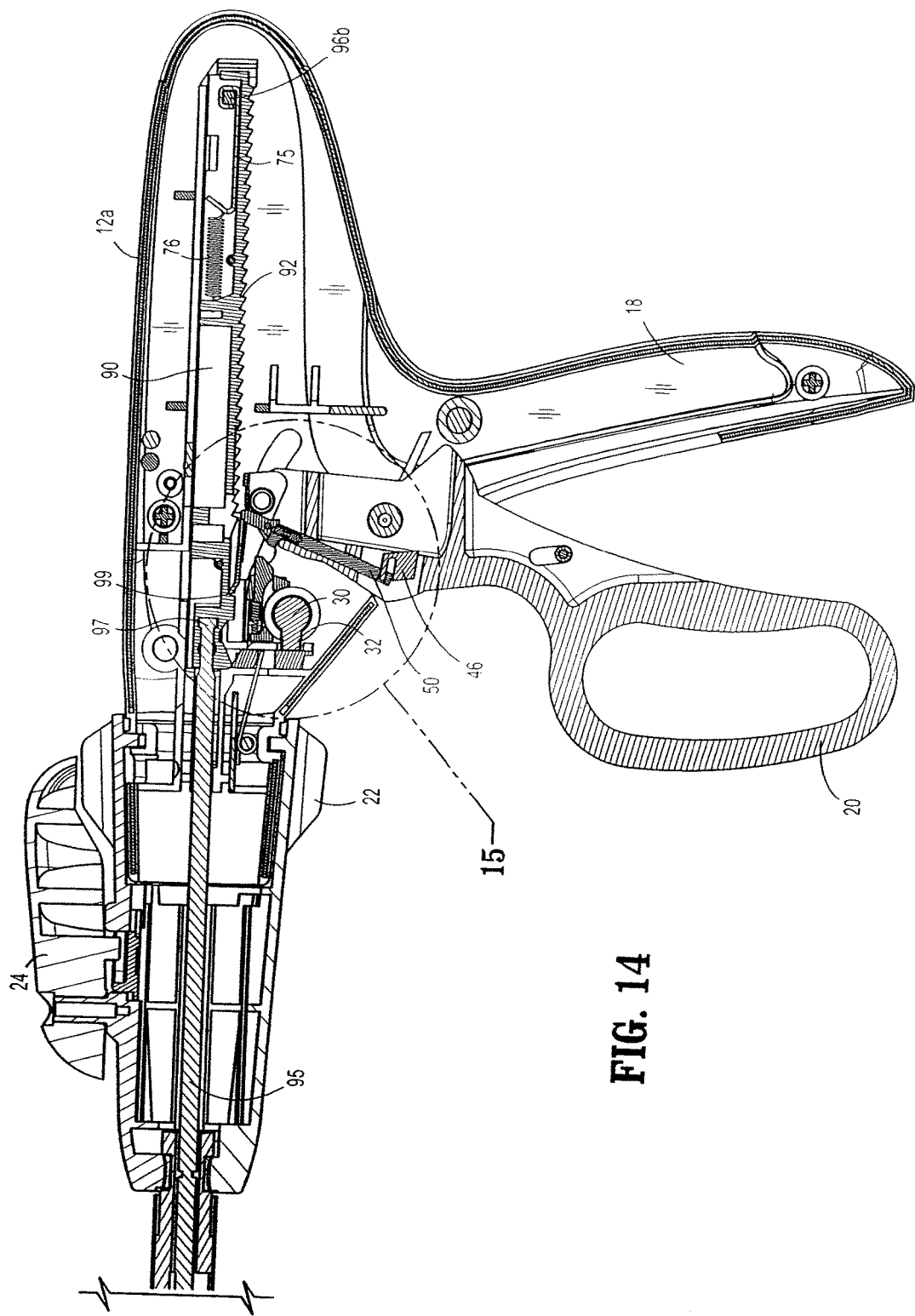
FIG. 14 is a side cross sectional view of the handle assembly of FIG. 1.

FIG. 14 illustrates operation of the retraction mechanism of device 10. In use, when retractor knobs 15 are pulled rearwardly by a surgeon, coupling rod 96 initially moves release plate 70 rearwardly in relation to actuation shaft 90 as coupling rod 96 slides in slots 98 of actuation shaft 90 such that pins 91 cam release plate 70 downwardly to a position covering toothed rack 92 of actuation shaft 90 and disengaging finger 125 of pawl 120 from toothed rack 92. When coupling rod 96 is pulled rearwardly to a position at which it engages the back end of slots 98, additional rearward movement of retractor knobs 15 will effect proximal movement of actuation shaft 90 and control rod 95.

Figure 20:
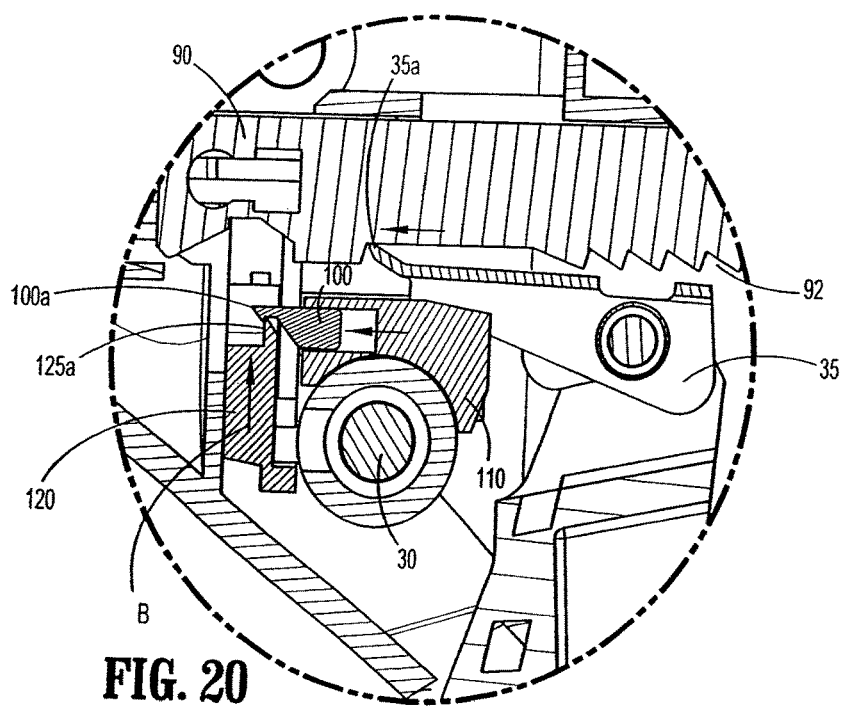
FIG. 20 is a side cross-sectional view, illustrating the vertical pawl biased into the downward position by the locking cam.

Device 10 starts out in grasping mode, per FIGS. 19 and 20. Movable handle 20 can be moved back and forth to open and close the jaws of tool assembly 27. Vertical pawl 120 is disengaged from toothed rack 92 and grasping pawl 60 is engaged in slot 92b.

Sliding slide buttons 40, 45 down moves grasping pawl 60 away from slot 92b and pawl arm 50 away from cam member 100 of locking cam assembly 107. When movable handle 20 is manipulated to clamp tissue, grasping pawl 60 moves into slot 92a such that vertical pawl 120 engages cutout 93. Plunger 30 is pushed and releases vertical pawl 120. When movable handle 20 is manipulated, advancement pawl 35 advances toothed rack 92, firing staples. Multiple strokes of movable handle 20 are used to advance toothed rack 92, with advancement pawl 35 repeatedly engaging and disengaging toothed rack 92. Yoke 80 maintains slide buttons 40, 45 in the upward position during firing. After retractor knobs 15 are used to retract toothed rack 92, grasping pawl 60 is aligned with slot 92b and device 10 is in the grasping mode again.

In an alternative embodiment, surgical stapling device 10 may be provided with a grasping mode, but without plunger 30. In this embodiment, vertical pawl 120 and locking cam assembly 107 are removed.

Device 10 starts in grasping mode, per FIGS. 19 and 20. Movable handle 20 can be moved back and forth to open and close the jaws of tool assembly 27 as grasping pawl 60 is engaged in slot 92b. Vertical pawl 120 and locking cam assembly 107 are removed in this embodiment.

Sliding slide buttons 40, 45 down moves grasping pawl 60 away from slot 92b. When movable handle 20 is manipulated to clamp tissue, grasping pawl 60 moves into slot 92a. As movable handle 20 is further manipulated, advancement pawl 35 advances toothed rack 92 and fires staples. Multiple strokes of movable handle 20 are used to advance toothed rack 92, with advancement pawl 35 repeatedly engaging and disengaging toothed rack 92. Yoke 80 maintains slide buttons 40, 45 in the upward position during firing. After retractor knobs 15 are used to retract toothed rack 92, grasping pawl 60 is aligned with slot 92b and device 10 is in the grasping mode again.

It will be understood that various modifications may be made to the embodiments disclosed herein. For example, it is envisioned that the surgical stapling device disclosed may be used in association with other surgical devices, e.g., clip appliers, dissectors, electrosurgical sealing devices, etc. Further, the device may also include tool assemblies other than staplers or those devices which eject a fastener, e.g., sealing devices (electrosurgical and non-electrosurgical), etc. The button or other actuator for changing the mode of operation for the device may be provided on one side or both sides of the handle assembly. Therefore, the above description should not be construed as limiting, but merely as exemplifications of preferred embodiments. Those skilled in the art will envision other modifications within the scope and spirit of the claims appended hereto.

What is claimed is:

1. A surgical device comprising:
   a handle assembly including an actuation shaft and a movable handle, the movable handle being operably associated with the actuation shaft such that movement of the movable handle effects axial movement of the actuation shaft;
   a switch on the movable handle, the switch having an original position;
   a grasping pawl on the movable handle, the switch moving the grasping pawl between a first position engaging the actuation shaft and a second position disengaged from the actuation shaft, the actuation shaft moving with movement of the movable handle; and
   a yoke for moving the position of the switch to its original position.

2. The surgical device according to claim 1, further comprising:
   a vertical pawl biased upwardly into engagement with the actuation shaft to prevent movement of the actuation shaft; and
   a disconnect mechanism movable into and out of engagement with the vertical pawl, the disconnect mechanism moving the vertical pawl away from the actuation shaft when the disconnect mechanism moves into engagement with the vertical pawl;
   the disconnect mechanism including a member that moves with the movable handle to automatically move the vertical pawl away from the actuation shaft with movement of the movable handle.

3. The surgical device according to claim 1, further comprising a cartridge assembly and anvil assembly, the cartridge assembly having a plurality of surgical staples.

4. The surgical device according to claim 3, wherein the cartridge assembly and anvil assembly are moveable back and forth between open and closed positions in a first mode of operation, and the cartridge assembly and anvil assembly clamp tissue in a second mode of operation, and wherein the switch is in its original position in the first mode of operation.

5. The surgical device according to claim 1, further comprising an elongated member extending distally from the handle assembly, the elongated member defining a longitudinal axis.

6. The surgical device according to claim 1, wherein the actuation shaft has teeth and further comprising an actuation pawl that engages and disengages the teeth in an alternating fashion, the actuation pawl being attached to the movable handle.

7. The surgical device according to claim 6, wherein the actuation pawl engages and disengages the teeth in an alternating fashion to effect the axial movement of the actuation shaft.

8. The surgical device according to claim 7, wherein the axial movement of the actuation shaft clamps tissue between a cartridge assembly and an anvil assembly.

9. The surgical device according to claim 7, wherein the grasping pawl moves a cartridge assembly and an anvil assembly between open and closed positions when the grasping pawl is in the first position.

10. The surgical device according to claim 1, further comprising a vertical pawl for retaining the position of the actuation shaft.

* * * * *